United States Patent [19]

Jöbsis

[11] 4,281,645
[45] Aug. 4, 1981

[54] METHOD AND APPARATUS FOR MONITORING METABOLISM IN BODY ORGANS

[75] Inventor: Frans F. Jöbsis, Durham, N.C.

[73] Assignee: Duke University, Inc., Durham, N.C.

[21] Appl. No.: 810,777

[22] Filed: Jun. 28, 1977

[51] Int. Cl.³ .............................................. A61B 5/00
[52] U.S. Cl. .................................................... 128/633
[58] Field of Search ................. 128/2 R, 2 L, 2.05 F, 128/2.05 P, 2.05 V, 633, 634, 664, 665, 2.06 R; 356/43–45, 39, 432

[56] References Cited

U.S. PATENT DOCUMENTS

| | | | |
|---|---|---|---|
| 3,463,142 | 8/1969 | Harte | 128/2 L |
| 3,626,932 | 12/1971 | Becker | 128/2.06 R |
| 3,638,640 | 2/1972 | Shaw | 128/2 L |
| 3,647,299 | 3/1972 | Lavallee | 128/2 L |
| 3,674,008 | 7/1972 | Johnson | 356/432 |
| 3,677,648 | 7/1972 | Dorsch | 356/40 |
| 3,811,777 | 5/1974 | Chance | 128/2 L |
| 3,825,342 | 7/1974 | Lubbers et al. | 356/41 |
| 3,830,222 | 8/1974 | Chance | 356/39 |
| 3,998,550 | 12/1976 | Konishi et al. | 128/2 L |
| 4,077,399 | 3/1978 | Le Roy | 128/2 L |
| 4,086,915 | 5/1978 | Kofsky et al. | 128/2 L |

OTHER PUBLICATIONS

Zijlstra, "A Manual of Reflection Oximetry", Van Gorcum's Medical Library, No. 152, 1958, Assen, Netherl.
Elam et al., "Annals of Surgery", vol. 130, 1949, pp. 755-773.
Wood et al., "Journal of Laboratory & Clinical Medicine", vol. 34, 1949, pp. 387-401.
Enson et al., "Journal of Applied Physiology", vol. 17, 1962, pp. 552-558.
Geddes et al., "Principles of Applied Biomedical Instrumentation", 1966, pp. 85-91.
Millikan, "Review of Scientific Instruments", vol. 13, Oct. 1942, pp. 434-444.
Goodman et al., "Lasers in Medicine", Gordon & Breach Science Publishers Inc., New York, London, Paris, pp. 373-374.
Goldman, "Biomedical Aspects of the Laser", Springer-Verlag, 1967, Berlin, Heidelberg, New York.
Lee et al., "IEEE Transactions on Biomedical Engineering", vol. 22, No. 3, May, 1975, pp. 248-249.

*Primary Examiner*—William E. Kamm
*Attorney, Agent, or Firm*—B. B. Olive

[57] ABSTRACT

A spectrophotometric transillumination method and apparatus are directed to non-invasive, continuous, atraumatic, in vivo, in situ monitoring of metabolism in a body organ. In the described applications, measuring and reference wavelengths within the near infrared region, i.e., 700–1300 nm, are utilized for non-invasive, continuous, atraumatic, in situ, in vivo monitoring of oxidative metabolism by monitoring oxygen sufficiency in an internal organ, e.g., the brain or heart, of a human or animal body. Advantage is taken of the critical characteristic of cellular enzyme cytochrome a, $a_3$ within the optical path and within the radiated portion of the selected organ for absorbing the selected measuring wavelength and for light of this measuring wavelength, as well as at least one reference wavelength within the same defined infrared region and at a low, non-hazardous level of intensity to travel through and be detectable at the end of a relatively long path, e.g., of several centimeters length, which may include substantial content of bone as well as soft tissue. The selection of wavelengths, circuitry and method also provide techniques for compensating for changes in blood volume in the organ being monitored, for continuous monitoring of hemoglobin oxygenation and blood volume and for intermittent monitoring of blood flow rate.

67 Claims, 16 Drawing Figures

METHOD AND APPARATUS FOR MONITORING METABOLISM IN BODY ORGANS

The invention described herein was made in the course of work under a grant or award from the Department of Health, Education and Welfare.

BACKGROUND OF THE INVENTION

1. Field of the Invention

The invention pertains to a method and apparatus for monitoring organ metabolism and is illustrated by method and apparatus directed to monitoring cellular oxidative metabolism by conducting non-invasive, in vivo, in situ measurements of changes in the steady state oxidation-reduction of cellular cytochromes together with changes in blood volume, the oxygenation state of hemoglobin and the rate of blood flow in the brain, heart, kidney, other organs, in limbs or other parts of a human or animal body.

2. History of the Prior Art

It is generally known that metabolism and more particularly oxygen sufficiency and adequacy of utilization are parameters of fundamental importance in assessing the function of any body organ. This is made self-evident when one considers that the energy provision for tissue function is underwritten for better than 94 percent by oxidative reactions involving the reduction of $O_2$ to $H_2O$. In the absence of sufficient oxygen, this process becomes impaired with a corresponding impairment in organ function. In instances of extensive oxygen deprivation, over a period of time the organ loses viability and as a result the individual often has the same fate.

Although all organs are adversely affected by oxygen insufficiency, perhaps the problem is most acute in the case of the brain because of its exquisite sensitivity with respect to oxygen demand and its complete dependence on oxidative metabolism for proper function and viability. For example, an absence of oxygen in the brain for more than a dozen seconds produces dysfunction and an absence for longer than a few minutes spells irreversible damage. A less acute impairment of oxygen availability leads to a gradual loss in brain function, especially with respect to the higher centers of the cerebral cortex.

Because of the vital role that oxygen sufficiency plays in human physiology, intensive efforts have been made over the years to measure this parameter in various organs and most particularly in connection with the assessment of brain and heart function. However, a capability for direct measurement of the parameter in the intact brain, heart or any other organ by a non-invasive means has not previously been available. The prior methods have all been of a secondary nature (e.g., electroencephalographic changes during hypoxia) or indirect and traumatic (e.g., blood flow measurements).

At present, electroencephalograph recordings indicating dysfunction are mainly useful for diagnosis of severely hypoxic or anoxic conditions in the brain. Similarly, electrocardiograph recordings are used to establish an oxygen deficiency in the heart muscle. However, such methods are diagnostic only in far-advanced situations and the organ and patient are both in a precarious state before these signals become indicative of pathology.

Measurements of cerebral blood flow and more recently of myocardial blood flow are predicated on the assumption that insufficient circulation is the main cause of inadequacy of oxygen delivery to the tissues. Although this assumption is probably correct in the majority of cases, the fact remains that the method is indirect, beclouded by possibilities of arterial-venous (A-V) shunting and unable to distinguish inadequate micro-regional bloodflow especially when accompanied by macro-regional changes.

Local blood flow measurement is presently accomplished by means of radioactive materials incorporated in the blood supplying the organ in question during monitoring of local radioactivity of the patient. Administration is either by inhalation of a radioactive isotope of a gas or by arterial or venous injection of a solution containing such a gas. The gas must have sufficient solubility to be easily dissolved in the blood and tissues and its isotope must have sufficiently strong radiation to penetrate the overlying tissue to be externally monitored. Commonly, $^{133}$Xenon is employed for this purpose.

The method most commonly used is the wash-out technique after a bolus of $^{133}$Xenon containing solution is administered intraarterially or after breathing a gas mixture containing $^{133}$Xenon until a certain degree of saturation of the cerebral tissue has been accomplished. Blood flowing into the lungs will rapidly eliminate the $^{133}$Xenon from the blood, arterial levels will drop precipitously and from thereon the tissue $^{133}$Xenon levels will be washed out by equilibration with Xenon-free arterial blood. The rate of this process is mainly determined by the rate of blood flow through the observed area. Usually, several compartments with different time courses will be observed, the first being the blood itself, others being various fractions of tissue with different circulatory parameters. From these wash-out curves, which take many minutes to be completed, the rate of blood flow in the tissue (or tissues) is then calculated. Deductions about possible circulatory deficiencies are made and translated into further deductions concerning possible deficiencies of oxygen delivery to the tissue. Aside from the indirect nature of the information obtained, serious drawbacks exist in the need to expose the patient to radioactivity.

In yet another procedure, the arterial-venous (A-V) difference technique has been used in efforts to assess the uptake of oxygen across intact organs. This method depends on measuring the difference between oxygen concentration in the arterial blood supplying the tissue and the venous blood returning from it.

When used in brain studies, for example, a sample of arterial blood is drawn from a peripheral artery and a sample of venous blood returning from the head is obtained by means of a hypodermic needle which is inserted into the jugular bulb of the neck. Also, in order to calculate the rate of oxygen uptake, the total rate of blood flow must be measured. Aside from the fact that the measurement is contaminated with oxygen uptake from structures of the head other than the brain, the method is traumatic and incurs a degree of risk by the need for penetrating the jugular bulb. Moreover, measurements on myocardial oxygen uptake are precluded since pure venous blood from the heart muscle cannot be obtained routinely.

Oximetry techniques have been widely employed for monitoring the arterial blood oxygenation in general. However, such techniques are not directed to providing information primarily concerned with organ or cellular metabolism and more specifically with oxidative metabolism. While oximeter constructions and techniques employed in oximetry are believed to be widely known among those skilled in the art, reference to the same may be found in the book "A MANUAL OF REFLECTION OXIMETRY", W. G. Zijlstra, M.D., 1958, Koninklijke Van Gorcum & Comp. N.V., Assen, Netherlands. A useful background in the literature can be found in the following articles:

(1) Review of Scientific Instruments, Vol. 13, pgs. 434-444, 1942;

(2) Principles of Applied Biomedical Instrumentation, L. A. Geddes & L. E. Baker, pgs. 85-91, 1968; (3) Journal of Applied Physiology, 17: pgs. 552-558, 1962; (4) Journal of Laboratory and Clinical Medicine, 34: pgs. 387-401, 1949; (5) Annals of Surgery, 130: pgs. 755-773, 1949.

Transillumination of tissues by a laser beam of visible or near visible light at a low, non-hazardous power level not sufficiently intense to cause a reaction of the tissue is discussed in U.S. Pat. No. 3,769,963. Also, this patent illustrates in FIG. 1 of the patent use of such a non-hazardous light source as a probe for transillumination over what would appear to be a relatively long optical path possibly including both bone and tissue. Transillumination with an intense, incoherent light source as a diagnostic procedure is described on page 373 of the book "LASERS IN MEDICINE", Leon Goldman, M.D. and R. James Rockwell, Jr., 1971, Gordon and Breach, Science Publishers, Inc. New York, New York. The chapter of this book entitled "Laser Biology" also provides useful background. Laser transillumination as a diagnostic technique is also discussed at page 130 of the book "BIOMEDICAL ASPECTS OF THE LASER", Leon Goldman, M.D., 1967, Springer-Verlag New York Inc. What can be seen from these references is that transillumination over relatively long optical paths including bone and tissue can be achieved. However, none of such references are directed to the objectives or achievements of the present invention, namely that of using a relatively non-intense, relatively low power level, coherent light source within the near infrared region as a non-invasive means and method of continuously measuring body organ metabolism in vivo, in situ and atraumatically.

Circuitry for establishing periodically recurring reference and measuring light pulses and for measuring the transmitted, in vitro difference or intensity therebetween is illustrated in U.S. Pat. Nos. 3,799,672 and 3,804,535. Also, U.S. Pat. No. 3,804,535 teaches a type of feedback to the photomultiplier voltage supply as does U.S. Pat. No. 3,923,403. Mention of such feedback is made because the circuitry of the present invention utilizes a unique type of feedback in an in vivo, in situ, transillumination system to compensate for and monitor the blood volume changes in measurements of organ oxidative metabolism as compared to the reflectance-transillumination systems of the prior art described in the mentioned prior art which operate in vitro and generally produce no information related to in vivo, in situ oxidative metabolism as with the present invention.

Note should also be made with reference to U.S. Pat. No. 3,804,535 to the fact that employment of a reference signal related to an isobestic point, i.e., at which absorbance of oxygenated and deoxygenated (or "disoxygenated") blood are equal, has been known as a technique for revealing absorption characteristics of a measuring signal at another wavelength. However, this technique has not heretofore been employed as a means for compensating for blood volume changes in an in vivo, in situ transillumination system designed to measure cellular and organ oxidative metabolism.

A further aspect of the prior art to be appreciated is the application of the so-called Beer-Lambert Law for determining optical density by determining circuit parameters from the two conditions, namely of the light being transmitted directly without passing through the test subject as compared to the light being transmitted through the test subject. Various literature sources discuss how this law is applied, one such source being the above-mentioned U.S. Pat. No. 3,923,403.

An appreciation of how various combinations of measuring and reference wavelengths have been applied in the prior art for physiological measurements is also deemed useful to an appreciation of the present invention. In this regard, U.S. Pat. Nos. 3,704,706; 3,709,672; 3,804,535; 3,807,390; 3,831,030 and 3,910,701 may be referred to for background examples of various singular and multiple wavelength combinations, some of which reside within the near infrared region of interest to the present invention. However, what can be noted with reference to all such prior art is that none of the methods or circuitry apparatus therein disclosed provide means for in vivo, in situ monitoring of metabolism and more specifically of cellular oxidative metabolism of an internal organ as with the present invention.

Thus, it becomes apparent that while circulatory-respiratory functions, arterial blood oxygenation and blood samples, per se, have been monitored by photometric techniques, presently existing method and apparatus are not suited for assessing the sufficiency of oxygen and metabolism in general in such vital organs as the brain and heart. Further, such prior methods and apparatus do not provide precise information and are often traumatic as well. Consequently, an obvious need exists for a method and apparatus by which this life sustaining parameter, i.e., cellular oxidative metabolism, can be measured in vivo, in situ and monitored continuously with precision and in a non-invasive, non-traumatic manner. Equally important is a need to be able to monitor blood volume and blood flow rate of the organ being monitored.

SUMMARY OF THE INVENTION

It is known that the cellular enzyme cytochrome a, $a_3$ (also known as cytochrome c oxidase) has a key role in oxidative metabolism. That is, it has been established that the enzyme interacts directly with oxygen and mediates the release of energy during the reduction of $O_2$ to $H_2O$. This is achieved by the catalytic donation of four electrons to $O_2$ and subsequent combination with four H+ ions. Under conditions of an inadequate $O_2$ supply, electrons accumulate and the enzyme population shifts to a more reduced steady state. Consequently, an ability to continuously measure and monitor the redox state of this oxygen utilizing enzyme in vivo, in situ would provide decisive information on the parameter of oxygen sufficiency in any tissue or organ in question. The present invention provides that capability as well as the capability to monitor blood volume and blood flow rate in a manner which is non-invasive and atraumatic.

This is accomplished by optical techniques, the application of which has been made possible by observing that the body and its organs are relatively pervious to low level, non-hazardous light energy in the near infrared region of the spectrum. Of particular importance, it has been discovered that a beam of relatively low level, non-intense radiation in reference and measuring wavelengths of from about 700–1300 nm can penetrate, be transmitted through and be detected and monitored at the end of a relatively long optical path in any selected portion of a human or animal body, which path includes bone as well as soft tissue.

By fortunate coincidence, cytochrome a, $a_3$ has radiation absorption properties in the aforenoted spectral region, the character of which varies according to its oxidation state. Thus, the present invention recognizes that it is possible to monitor the redox state of this oxygen utilizing enzyme by a spectrophotometric method and apparatus not previously known to the art.

The spectrophotometric measurements, according to the invention, are made in vivo by transmitting near infrared radiation in at least two different and periodically recurring wavelengths through the test organ, in situ, and detecting and measuring the radiation intensity which emerges on the opposite side for assessment of biochemical reactions utilizing the previously-mentioned Beer-Lambert Law. One of the wavelengths selected is in a range at which oxidized cytochrome a, $a_3$ is highly absorptive. One or two additional wavelengths outside the peak of the cytochrome absorption band, but preferably in relatively close proximity to the measuring wavelength are presented in sequence to provide one or more reference signals. A simple subtraction or ratio calculation between the measuring and reference signals is achieved by appropriate circuitry and the non-specific changes in the intensity of transmitted radiation not attributable to absorption by cytochrome a, $a_3$ are eliminated.

Although the capability for continuously monitoring cellular oxidative metabolism by monitoring the redox state of cytochrome a, $a_3$ in the cells of the selected organ is of principal interest, ancillary data on circulatory parameters related to functioning of the organ can also be obtained in accordance with the techniques of this invention. For example, the oxygenation state of the blood supplied to a given organ can be monitored by the hemoglobin band at slightly different wavelengths, e.g. 740–780 nm, in the aforenoted near infrared region of the spectrum. Likewise, data on the total blood volume of the organ can be obtained by monitoring a hemoglobin (Hb) oxyhemoglobin ($HbO_2$) isobestic point. This well-known spectrophotometric term refers to a wavelength at which two forms of the same molecule or mixture of molecules have equal absorption intensity. Thus, for oxygenated and disoxygenated hemoglobin, such a point is found to occur variously between 810 and 820 nm. This variation of stated wavelengths derives from problems arising from the very low optical densities of Hb and $HbO_2$ in this range and the relative insensitivity of most commonly available spectrophotometers in this wavelength range. In practice, any wavelength in the entire range of 815±5 nm can be used without jeopardy to the results in situations where the measurements are less sensitive to small errors. A yet wider range of wavelengths can serve the purpose since even small blood volume changes will outweigh the possible interference by $Hb \rightleftharpoons HbO_2$ shifts. In another approach, the less practiced technique of combining two wavelengths with opposite optical density (OD) responses to the interfering reaction can be combined. Thus, for $Hb \rightleftharpoons HbO_2$ equal $\Delta OD$ values but of opposite sign occur at 788 and 870 nm. This combination of signals of equal strength but opposite sign at two wavelengths is called a "contrabestic pair". It is especially useful when two reference wavelengths are used straddling the peak to be measured in conditions of intense and changing, wavelength dependent scattering. A series of wavelengths chosen such that the net sum of their optical density changes becomes zero is another method of practicing the cancellation of interfering reactions. In contradistinction, "equibestic" pairs can be used to correct for errors arising when the spectral effects of a Hb to $HbO_2$ shift or the reverse predominate. In this case a reference wavelength is selected which has an equal OD effect in the same direction as the one occurring at the measuring wavelength when the interfering reaction proceeds.

In addition, blood flow rates may be monitored, albeit discontinuously, by the rapid administration of a small quantity of a dye, e.g., "cardiogreen", having absorption properties in the near infrared spectral region or alternatively by having the test subject take single breaths of a gas mixture containing a high and low concentration of oxygen in alternating sequence or one breath of a mixture with a small, innocuous admixture of CO. By selecting two wavelengths for differentially measuring the optical density of the organ in the spectral region of the absorption band of the dye, an optical signal indicating the arrival and subsequent departure of the dye in the cerebral circulation and dilution in the total blood volume, the so-called transit time, is measured. The latter is directly indicative of the rate of blood flow as proven by Zierler (see the book "PRINCIPLES OF APPLIED BIOMEDICAL INSTRUMENTATION"). Similarly, the optical density differences of the hemoglobin compounds ($HbO_2$, HbCO or other) can be used to provide the optical signal when the inspired air is suddenly and briefly varied.

DESCRIPTION OF THE DRAWINGS

A better understanding of the invention may be had by reference to the detailed description which follows, taken in conjunction with the accompanying drawings, in which.

DETAILED DESCRIPTION OF THE INVENTION

Figure 1:
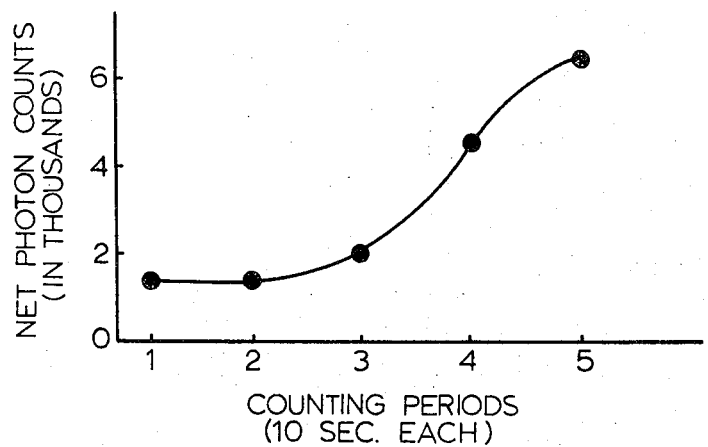
FIG. 1 is a graphical representation of optical density changes in the human brain at 815 nm in vivo plotted against time periods according to the invention during which a progressing cerebral ischemia occurred as a result of hyperventilating the respiratory system.

A salient feature of the present invention is the observation that light energy in the near infrared region having wavelengths in the range of from about 700–1300 nm and at a relatively low, non-hazardous density can be made to penetrate both soft tissue and bone surrounding a living organ and in a relatively long optical path and the detected light at the end of the path can be related to oxidative metabolism. This wavelength range has also been proven critical since within the 700 to 1300 nm wavelength range oxygenated hemoglobin (HbO$_2$) has extremely low absorption characteristics, whereas disoxygenated hemoglobin (Hb) displays some weak absorption which slowly rises with decreasing wavelengths below 815 nm to a small peak in absorption around 760 nm. Because of these optical properties, the Hb-HbO$_2$ steady state (i.e., the venous-arterial average) can be monitored.

In addition and of significant importance, the invention recognizes that cytochrome a, a$_3$ in living body tissue also exhibits an oxygen dependent absorption band in the 700 to 1300 nm wavelength range of the spectrum. When this key enzyme in oxidative reactions is in the presence of sufficient oxygen, a weak absorption band exists in the 780 to 870 region with a maximum at a wavelength of about 820 to 840 nm. The absence of oxygen results in a complete reduction of the enzyme and a concomitant disappearance of the absorption band.

Cytochrome a, a$_3$ is the terminal member of the mitochondrial respiratory chain and functions as a donor of four electrons to molecular oxygen in the final step of the main pathway of oxidative metabolism in the cells. In this reaction, the electrons are transferred to oxygen from the four metallic redox components of the enzyme, the two iron atoms of the a and a$_3$ hemes and two copper atoms. Subsequent or concomitant combination with four hydrogen ions leads to the formation of H$_2$O. The free energy difference between the hydrogens in the metabolic substrates and in H$_2$O is partially conserved in the form of high energy phosphate bonds through the oxidative phosphorylation of adenosine diphosphate (ADP) to adenosine triphosphate (ATP). The latter compound serves as the primary free energy carrier in the cell and meets the free energy needs of most of the endergonic reactions required for normal physiological function and cell survival. Since better than 90 percent of cellular ATP production is by means of oxidative phosphorylation and since oxygen utilization is governed by the rate of transfer of electrons to oxygen from cytochrome a, a$_3$, this enzyme performs a critical role in cellular oxidative metabolism and energetics. In the absence of sufficient O$_2$, electrons accumulate in cytochrome a, a$_3$, producing a more reduced steady state. Thus, the invention recognizes that direct measurements on the redox state of this enzyme will provide conclusive data on the adequacy of oxygen availability and its utilization in living tissue and organs.

In carrying out a continuous, non-invasive, in vivo, in situ monitoring of the redox state of cytochrome a, a$_3$, near infrared radiation of appropriate wavelengths and at a relatively low power level and corresponding relatively low density is presented at one side and is transmitted through the organ under investigation, and the light emerging from the opposite side is conducted to a photomultiplier tube for detection and measurement.

The monitoring may be conducted in either a dual or triple wavelength mode with one of the wavelengths being selected to provide a measuring signal and the others a reference signal. The measuring wavelength is preferably at about 840 nm, the center of the cytochrome a, a$_3$ absorption peak observed in vivo, but the choice is not so limited since other wavelengths in the absorption band can be utilized.

By calculating the difference between the measuring and reference signals, the non-specific changes in transmission characteristics not attributable to cytochrome absorption are in effect cancelled out. Appropriate electronic circuits are used to amplify and demodulate the separate signals, convert them to DC current and subtract them for a differential recording.

In one version of the dual mode, the isobestic point of Hb-HbO$_2$ at 815 nm ±5 nm is used as the reference wavelength with a feedback control on the signal produced to compensate for changes in blood volume. That is, a negative feedback circuit connected to the high voltage source which supplies the photomultiplier tube is used to compensate the reference signal for changes in the reference signal level caused by blood volume changes in the tissue being monitored. The voltage adjustment is then maintained in the subsequent interval when the measuring wavelength is transmitted. Since the changes in voltage supplied to the photomultiplier are directly proportional in magnitude to the changes in blood volume over the optical path, in effect they measure this important circulatory parameter and are recorded.

In the triple wavelength mode three wavelengths are presented, i.e., the measuring wavelength and two reference wavelengths. Desirably, the reference wavelengths straddle the measuring wavelength and are in relatively close proximity to it. A suitable choice would be for one reference wavelength to be about or less than, say, 75 nm lower than the measuring wavelength and the other to be about 75 nm higher. When interference by blood volume changes is present, resort is made to a contrabestic pair for the two reference wavelengths. When Hb⇌HbO$_2$ changes predominate over blood volume changes an equibestic pair is employed.

As has been noted supra, hemoglobin also possesses oxygen dependent absorption properties in the near infrared region of the spectrum which permits continuous monitoring of the Hb-HbO$_2$ steady state. In practice, advantage is taken of the fact that disoxygenated hemoglobin (Hb) exhibits a relatively weak absorption which slowly rises with decreasing wavelengths below 815 nm to a small peak in the vicinity of about 760 nm. Thus, determinations on the Hb-HbO$_2$ steady state can be made by differential measurements at wavelengths of about 760 nm and 815 nm, with the 815 nm wavelength (Hb-HbO$_2$ isobestic point) serving to provide the reference signal.

It is apparent from the above discussion that the method of this invention provides a capability for in vivo, in situ, non-invasive, atraumatic and continuous monitoring of three parameters of crucial significance related to organ metabolism and particularly in situations where information on the state of circulatory adequacy and oxygen sufficiency are needed. These parameters include:

1. The adequacy of oxygen availability for normal function of cytochrome a, a$_3$, the cellular enzyme which mediates better than 90 percent of the oxygen consumed in living tissue.

2. The total blood volume in the tissue under question; and

3. The steady-state status of the relative predominance of oxygenated arterial blood (HbO$_2$) and disoxygenated venous blood (Hb).

Additionally, it should be noted that blood flow rate may be monitored as previously set forth and related to the parameters mentioned, while monitoring of the enumerated three parameters may constitute separate methods of monitoring, the invention contemplates monitoring of plural parameters.

In a preferred embodiment, all three parameters are continuously monitored in a single system by a triple wavelength technique in which one reference and two measuring wavelengths are alternately presented to the tissue being tested at a rate (>30 Hz) providing sufficient time resolution for the monitoring of the most rapid metabolic reactions. An isobestic point of Hb-HbO$_2$ at a wavelength of 815 nm±5 nm is used to provide the reference signal that is subtracted from the measuring signal. One of the measuring wavelengths monitors the oxidized cytochrome a, a$_3$ peak at about 840 nm while the other provides a signal on the Hb-HbO$_2$ steady state by monitoring the disoxygenated hemoglobin absorption peak at around 760 nm. The choice of measuring wavelengths is not limited to 760 and 840 nm, since other wavelengths in the cytochrome a, a$_3$ and hemoglobin absorption bands are likewise applicable. However, wavelengths at about 760 and 840 nm are generally preferred. The feedback control on the reference signal compensates for blood volume changes and is used to monitor blood volume in the test tissue. That is, as previously explained, voltage changes in the feedback loop are recorded as measure of changes in blood volume.

The following experiments were carried out, among others, to demonstrate the capability of the in vivo, in situ, non-invasive, atraumatic methods described herein for achieving a continuous monitoring of oxidative and circulatory parameters in the intact organ of a physiologically functioning test subject.

EXPERIMENT I

Since the brain is most sensitively dependent on oxygen for normal function and readily accessible with minimal interference of overlying tissues, initial experiments were performed on the brain of a cat by transillumination of the intact skull and musculature and skin.

In preparation for the experiment, the animal was anesthetized with pentobarbital (40 mg/$_{kg}$), tracheotomized, intubated and provided with femoral arterial and venous cannulae. Hair was removed over an area of approximately two sq. cm. at both temples by a depilatory agent. The head, which measured 4.86 cm between temples, was immobilized in a stereotactic holder and a light conducting bundle of optic fibers was applied with firm pressure against the skin at each temple. One bundle transmitted the appropriate wavelengths of near infrared radiation as a beam of light from two monochromators to one temple, the other conducted the light emerging from the opposite side of the head to a photomultiplier tube for detection and measurement. The optical density at the point of entry at the temple was relatively low and was approximately $2 \cdot 10^{-5}$ watts per square centimeter which is currently accepted as being a non-hazardous level for human application. Two 6.6 nm spectral bands were presented alternately at a repetition rate of 60 Hertz. Sufficient light was received to be detected and monitored. Electronic circuits, such as previously referred to and further illustrated in FIGS. 5, 6 and 7, were employed to amplify and demodulate the separate signals, convert them to DC and subtract them for a differential readout. One wavelength band provided the reference signal and the other the measuring signal. For the reference wavelength, the isobestic point of Hb-HbO$_2$ in the 815 nm region was selected. A negative feedback circuit on the high voltage source supplying the photomultiplier compensated the reference signal for blood volume changes in the optical pathway. Since the voltage changes reflect changes in blood volume, they were recorded as an indicator of this parameter. In addition, means were provided for monitoring changes in femoral arterial blood pressure.

Although the aforenoted circulatory parameters were monitored, the principal purpose of the experiment was to obtain kinetic measurements on cytochrome a, a$_3$ and cerebral hemoglobin during a temporary condition of asphyxia induced by interruption of artificial respiration for a period of three minutes after paralysis of the animal under test. The results obtained, using an analog detection system, are shown in FIGS. 2 and 3 of the drawings.

Figure 2:
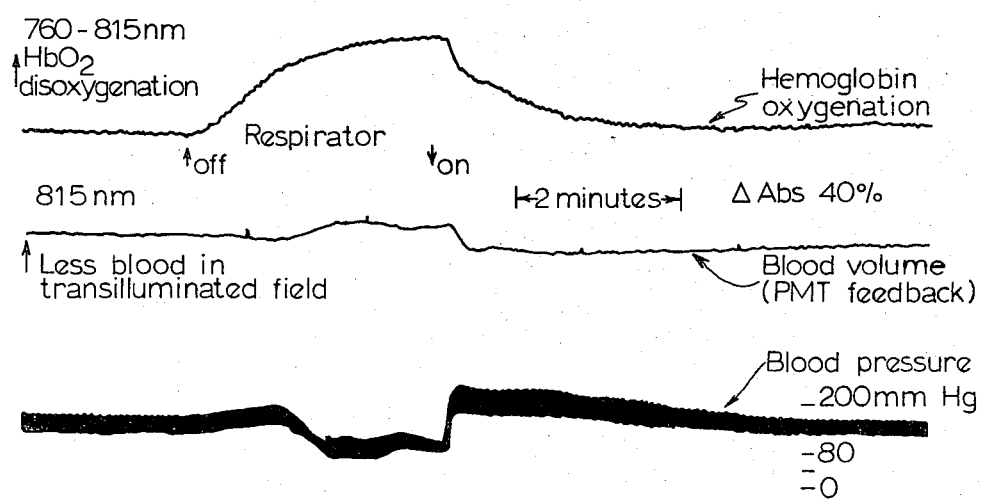
FIG. 2 illustrates changes in hemoglobin, blood volume and blood pressure brought about by changes in the radiation absorption characteristics of cerebral hemoglobin in the head of a cat during temporary asphyxia induced by interruption of artificial respiration for three minutes after paralysis of the aminal.

Referring to FIG. 2, the top trace shows the signal recorded for the 760-815 nm wavelength difference, and indicates the change of hemoglobin from a partially arterial (oxygenated) to a more venous (disoxygenated) condition. The middle trace represents the negative voltage supplying the photomultiplier tube after feedback stabilization for constant reference signal (815 nm). The rise in the trace indicates a decreasing optical density at this wavelength (Hb-HbO$_2$ isobestic point), which is seen to accompany the fall in blood pressure (lower trace). Apparently, a measurable decrease in cerebral blood volume occurs when the circulation starts to fail.

Figure 3:
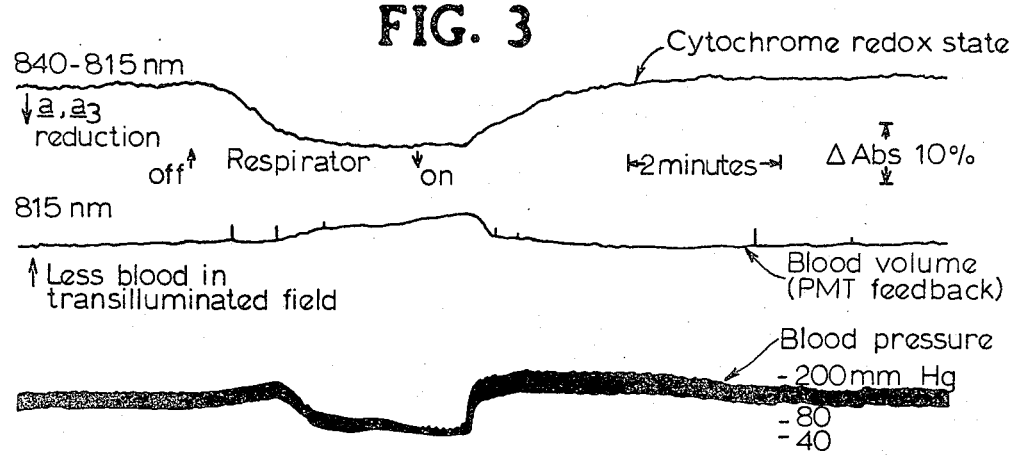
FIG. 3 shows the changes in the cytochrome enzyme from an oxidized to a reduced state, the change in blood volume and the change in blood pressure brought about by changes in the radiation absorption properties of cerebral cytochrome a, $a_3$ in the course of the same experiment on the cat test subject referred to in the above description of FIG. 2.

The reduction of cytochrome a, a$_3$ in the next hypoxic episode during the period of temporary asphyxia is shown in FIG. 3. It is seen that the 840-815 nm difference signal declines in intensity which indicates movement from the oxidized to the reduced state (top trace). It is also noted that after artificial respiration has been resumed, the cellular enzyme is returned to the oxidized state and the absorption properties characteristic of this state reappear. As in FIG. 2, the middle and bottom traces represent, respectively, the occurrence of changes in blood volume and blood pressure.

EXPERIMENT II

In this experiment, intra-cranial blood volume changes were continuously monitored on a human test subject in vivo, in situ, non-invasively and atraumatically. Voluntary hyperventilation, which decreases cerebral circulation by hypocapnia, was used as a functional test on a healthy, adult male having a larger than average head measurement (13.3 cm diameter at the temples).

In carrying out the experiment, a bundle of light conducting, optical fibers was firmly applied to each temple to provide a coherent light source. One bundle (having an area of 0.567 $cm^2$) transmitted light at a wavelength of 815 nm (the Hb-$HbO_2$ isobestic point) to one temple, while the other conducted the light emerging at the opposite temple to a photon counter for measurement. The optical density at the point of entry at the temple was relatively low and was approximately 48$\mu$ watts per square centimeter. Photon counting rather than the alternative analog technique was used in order to increase detection sensitivity. Sequential counting periods of ten seconds each were used with one second intervals interspersed between the counts for readout. Hyperventilation was started shortly before the beginning of the first counting period.

A significant decrease in optical density, reflected in increased net counts (total counts minus background) was observed as the counting periods progressed. This is shown graphically in FIG. 1 of the accompanying drawings. During the course of the experiment, the verbal comments of the test subject were noted, and it was found that they correlated with the recordings on photon counts. That is, at the beginning of the third counting period a feeling of dizziness was reported, at the fourth period a more intense dizziness, and at the fifth period the subject indicated that he was too dizzy to continue. Thus, the experiment demonstrates a successful, non-invasive, continuous, atraumatic monitoring in vivo, in situ of partial cerebral ischemia in a living human subject.

EXPERIMENT III

Figure 4A:
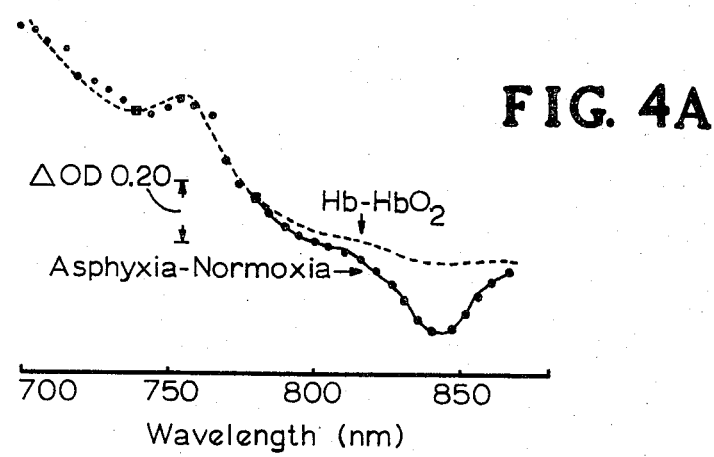
FIG. 4A shows a plot of optical density changes at a number of wavelengths performed on a cat by cranial transillumination, the dashed line trace representing the hemoglobin spectrum and the solid line trace representing the trend of the data diverging from the hemoglobin difference spectrum.
Figure 4B:
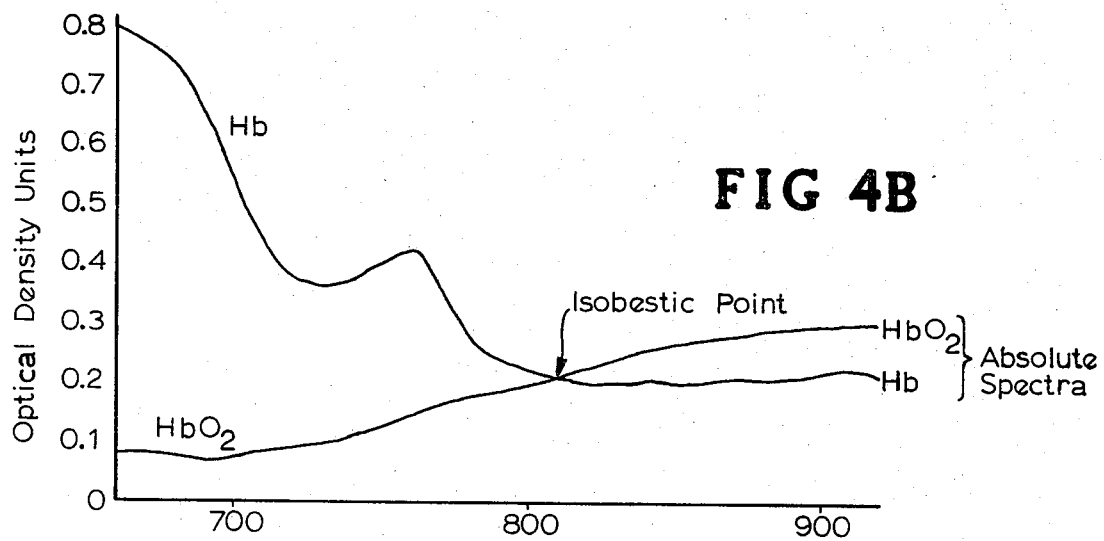
FIG. 4B illustrates the absolute absorption spectra of oxygenated hemoblobin ($HbO_2$) and deoxygenated hemoglobin (Hb).
Figure 4C:
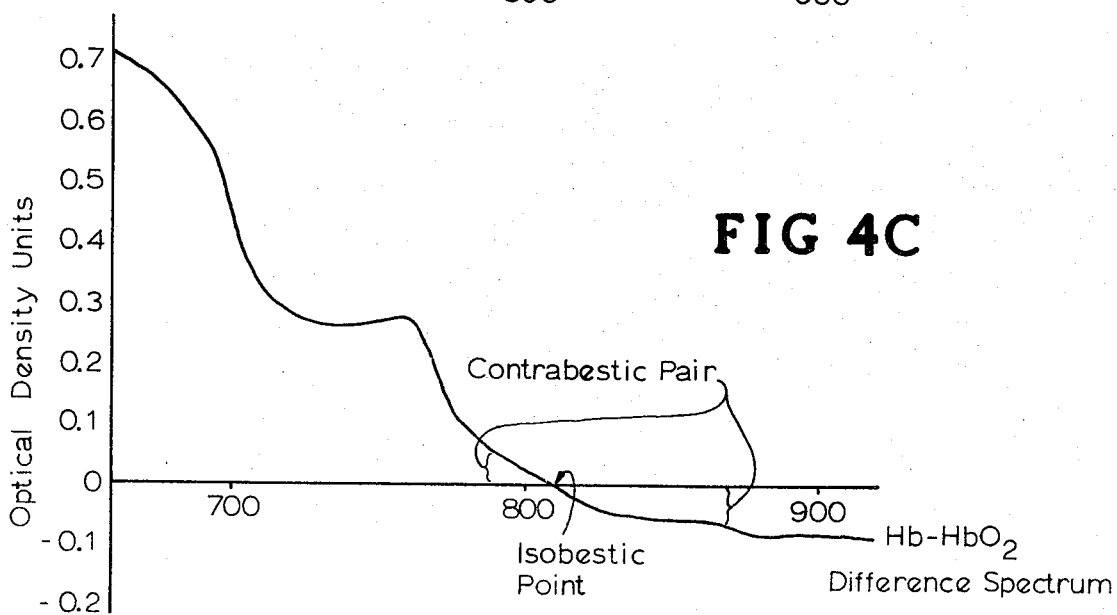
FIG. 4C shows the spectral differences observed when blood changes from HbO$_2$ to Hb, as was the case in the experiment of normoxia to anoxia illustrated in FIG. 4A.

When tissue becomes anoxic, for instance by a lack of oxygen in the blood supplying it, a comparison of the near infrared spectrum before and after the event should show a hemoglobin change towards the maximally disoxygenated form and the reduction of cytochrome a, $a_3$ should become evident. In FIG. 4A, the results are shown of such an experiment performed on a cat by cranial transillumination. The optical density changes at a number of wavelengths measured between the normally breathing, anesthetized animal and after death by asphyxiation are shown as dots. Using the 740 and 780 nm points for normalization, the hemoglobin spectrum form in vitro measurements was scaled accordingly and is depicted as a broken line. The derivation of these hemoglobin data is illustrated in FIGS. 4B and 4C. The solid line in FIG. 4A depicts the trend of the data where they diverge from the hemoglobin difference spectrum. The maximal difference at approximately 840 nm is identified as caused by the reduction of cytochrome a, $a_3$. It is seen that at 815±5 nm the contribution of cytochrome a, $a_3$ reduction is minimal and can be neglected when this Hb-$HbO_2$ isobestic point is used for feedback against blood volume changes.

RATE OF BLOOD FLOW

As previously noted, the rate of blood flow through a given organ may also be measured by the apparatus and methods of this invention. The 815 nm feedback signal can be used as a measuring signal, or alternatively, the signal obtained by presenting light of a wavelength in the range where hemoglobin has a more intense absorption such as between 740–780 nm. One technique has used arterial injection of a bolus of dye having absorption properties in the selected test wavelength. The time taken for the bolus to pass through the optical pathway is then used to calculate blood flow rate by the so-called transit time technique. In a more preferred variation of the procedure, the test subject inhales a single breath of air containing a small admixture of carbon monoxide. The period of time in which the optical signal is affected by the presence in the blood of the first and highest concentration of the hemoglobin-carbon monoxide compound passing through the optical pathway is evident from a decrease in optical density arising from the fact that the Hb-CO compound exhibits practically no light absorption properties in the near infrared range. The temporary decrease in optical density is used to calculate the blood flow rate by recording intensity and time interval, as described in the Zierler reference.

What the invention recognizes and what should be fully appreciated in the foregoing description is that the success of cerebral IR monitoring of oxygen sufficiency according to the invention depends upon the rate of oxidative metabolism and concomitantly the cytochrome content of extra cerebral tissues being very low in comparison with those of cerebral tissue. Because of this low concentration of cytochrome a, $a_3$ in skin and bone tissue and the short optical pathlength compared to the high cerebral cytochrome a, $a_3$ concentration and the long optical pathlength through the human brain, the total cytochrome a, $a_3$ signal upon transcranial illumination derives predominantly (better than 98%) from brain tissue. The same holds true for the distribution of the total volume of blood. Although the concentration of cytochrome a, $a_3$ in heart muscle is much higher yet, the relative optical path lengths through non-myocardial and myocardial tissue during transillumination of the chest produces a ratio of the same order of magnitude. Thus, a wide range of applications to monitoring of body organ metabolism generally, cellular metabolism and particularly cellular oxidative metabolism are suggested.

In addition to the naturally occurring compounds discussed so far, hemoglobin and cytochrome a, $a_3$, any other compound absorbing differentially in the near IR, depending on the metabolic or physiological function of the tissue, can be used for monitoring purpose of such functions. These other compounds may be either as yet unidentified naturally occurring ones or ones artificially introduced by ingestion or other administration. For one example, the use of indicator dyes having differential optical properties depending on the local pH is foreseen as a useful further application and extension of the technique since during $O_2$ deficiency the degradation of glucose to lactic acid (glycolysis) occurs and produces considerable shifts in tissue pH.

The present invention could also be used to great advantage in any clinical situation where the oxygen sufficiency of the brain, heart, or other organs, needs to be continuously monitored and studied. For example, such information is often of critical importance in the course of surgical operations, during treatment of patients in intensive care units and especially in the case of premature babies as has been previously recognized and discussed in U.S. Pat. No. 3,704,706. In the latter situation, the critical question is how much oxygen to give the premature baby. Too much can result in blindness and permanent lung damage, while too little ends in brain damage or death. Improvements in monitoring oxygen levels, such as provided by this invention, can greatly reduce these problems.

Attention will now be turned to further explanation of the circuitry and instrumentation which may be used in practicing the aforedescribed method of this invention.

INSTRUMENTATION

A portion of the instrumentation of the invention provides means for measuring the difference in transmitted optical intensity between periodically recurring reference and measuring light pulses of different wavelength detected by a photomultiplier tube. Since the prior art, e.g., U.S. Pat. No. 3,804,535, describes such a technique, the circuit description to follow will primarily be concerned with those aspects of the instrumentation directed to providing the unique array of reference and measuring wavelengths, the feedback circuitry which allows the received reference signal level to be monitored and compensated for blood volume changes in the organ under examination and the associated circuitry which allows the feedback regulated voltage to the detector or the regulating feedback voltage itself to be recorded as a measure of such blood volume change.

Figure 5:
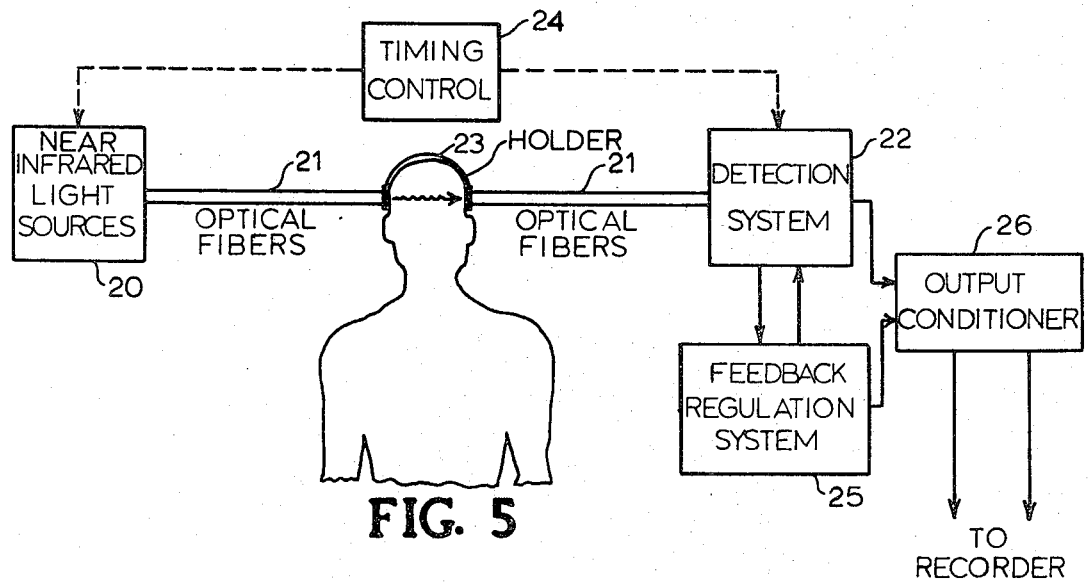
FIG. 5 is a generalized block diagram of a system of instrumentation employed in carrying out the monitoring techniques of the invention using analog circuitry.

A block diagram of the major component system of instrumentation and apparatus suited for continuous, atraumatic, non-invasive, in vivo, in situ infrared monitoring of internal oxidative metabolism ($O_2$ sufficiency) and circulatory parameters is illustrated in FIG. 5. The example shown is for transcranial illumination for cerebral monitoring.

The near infrared light sources 20 alternately present radiation through optical fibers 21 at different wavelengths, the intensity of which is measured by the detection system 22. A suitable holder 23 is employed to insure maximum transmission and minimum loss at the points of entry and exit and guard against involuntary displacements. Such a "holder" may, for example, simply consist of taping the light sources and receivers to the body or may follow an earphone type construction with means to clamp the light sources and receivers in the selected positions.

The timing control 24 controls the rate and sequence of the monochromatic flashes and demodulates the detected light signals. A feedback regulation system 25 allows the detected signal at one wavelength (e.g. a hemoglobin isobestic point) to be kept constant by negative feedback adjustment of the detector sensitivity to compensate for transmission changes brought about by changes in blood volume in the organ being examined during the time of transillumination. The detector sensitivity is then kept constant during the subsequent presentations of the monochromatic flashes at the other wavelengths. In the next cycle, this procedure is repeated. In addition to stabilization against blood volume changes, the feedback signal also provides information on these changes. The received reference and measuring signals as well as the feedback voltage blood volume indicating signal are all fed through output conditioner circuitry 26 and then to appropriate recording or display means, as later described. Note should again be taken that either the feedback regulated voltage to the detector or the regulating feedback voltage itself may be recorded as a measure of blood volume change.

The infrared light sources 20 may be either narrow spectral bands ("monochromatic light") derived from an incandescent or arc lamp by appropriate filters or monochromators or any of a number of wavelength specific light sources such as light emitting diodes (LED's) or diode lasers (LaD's) or other laser devices known to those in the art. The required power supplies and LED or laser pulse generators will, of course, be understood to be included as part of the light sources 20 and will be suited to relatively low power levels and non-hazardous optical densities as are suited to the invention. What is important to note here is that the invention recognizes the commercial availability of light sources suited to the invention and more particularly that such light sources in the particular reference and measuring wavelengths of the invention can be utilized in relatively long optical paths, in vivo, in situ at relatively long non-hazardous optical intensities and non-invasively for monitoring organ and cellular metabolism.

Figure 6:
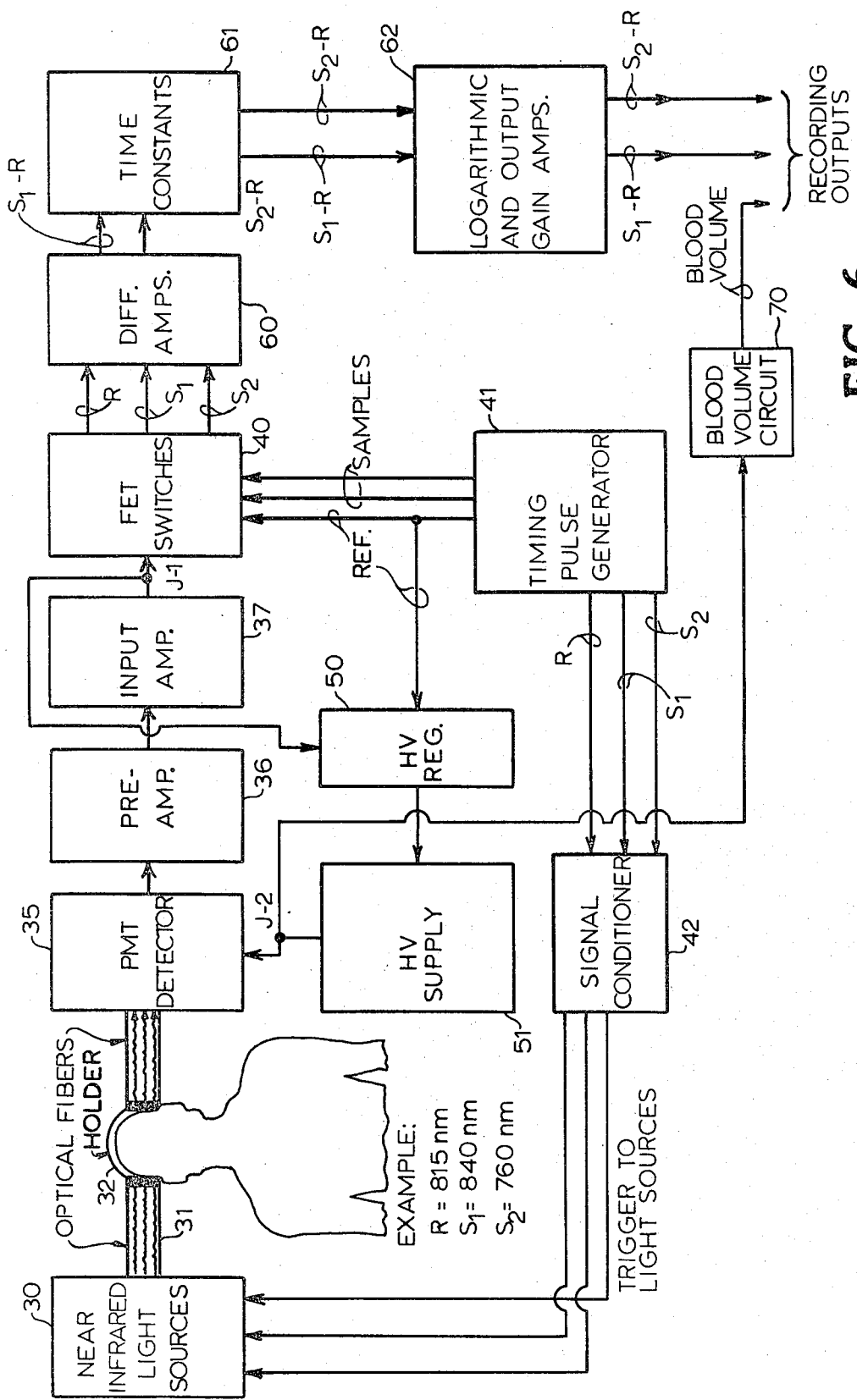
FIG. 6 is a more detailed block diagram of a system of instrumentation for carrying out the monitoring techniques of the invention.

FIG. 6 represents a somewhat more detailed block diagram of the circuitry and instrumentation apparatus of FIG. 5. FIG. 6, like FIG. 5, is selected to represent an analog circuitry system for transcranial illumination for cerebral monitoring and is intended to provide monitoring information in vivo, in situ, non-invasively and continuously related to the state of cellular oxidative metabolism of the brain of the subject being examined. Various combinations of wavelengths, selected according to the invention, have been previously discussed. The system of FIG. 6 is intended to represent, as an example, utilizing two measuring or "sample" wavelengths of 840 nm and 760 nm respectively (designated S-1, S-2) and a single reference wavelength of 815 nm (designated R). Note should again be taken here of the critical absorption characteristic of the enzyme cytochrome a, $a_3$ with respect to the wavelength 840 nm, the critical hemoglobin oxygenation characteristic exhibited at 760 nm and the fact that 815 nm represents an isobestic point. Thus, the redox state of cytochrome a, $a_3$, the state of hemoglobin oxygenation and blood volume are all measurable parameters.

In the embodiment of FIG. 6, it should be noted that further experience with the invention will indicate combinations of wavelengths other than those shown. It is, therefore, contemplated that instrumentation providing narrow bandwidths at many center wavelengths, e.g., at 10 nm intervals throughout the 740 to 890 nm range, will be employed according to the invention to establish other groups of reference and measuring wavelengths suited to the invention.

Continuing the description of FIG. 6, the light sources 30 having the three mentioned wavelengths of 760 nm, 815 nm and 840 nm, each preferably confined to a narrow (6 nm) band, transmit through optical fibers 31 and an appropriate holder 32 and provide a relatively low, non-hazardous optical intensity at the point of entry. Comparing FIG. 5 and FIG. 6, the detection system 22 shown generally in FIG. 5, is made up in FIG. 6 of a photomultiplier detector 35, a closely coupled preamplifier 36 and input amplifier 37 of conventional construction and connected as indicated in FIG. 6. This system transduces IR light energy into electrical signals.

The timing control 24 of FIG. 5 includes in FIG. 6 the FET switches 40, the timing pulse generator 41 and the signal conditioner 42, whose connections are as indicated in FIG. 6 and whose functioning provides means for separating the signals at the different wavelengths and for synchronizing the different wavelength presentations and the detection system. Such circuit components as such are well known, both as to construction and function. Equivalent devices could be used. For example, while FET (Field Effect Transistor) type switches 40 are suggested, any equivalent electronic switching means would be applicable. The three wavelengths, reference wavelength 815 nm, measuring or sample wavelengths 840 nm and measuring or sample wavelength 760 nm are thus presented, transmitted and detected as periodically recurring light pulses at a relatively low, non-hazardous level and are then separated out for measuring and monitoring purposes.

Figure 7:
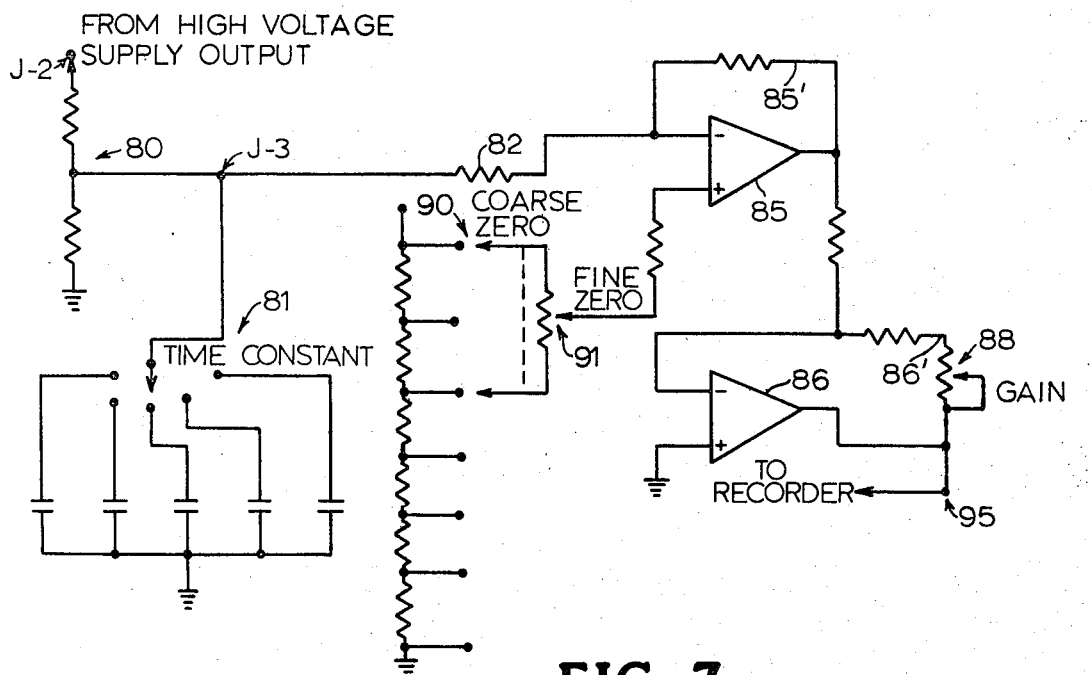
FIG. 7 is a detailed circuit diagram of a portion of the feedback circuitry used to provide information of changes in blood volume flow to the organ.

Continuing the description of FIG. 6, the feedback regulation system 25 of FIG. 4 includes in FIG. 6 a high voltage regulation circuit 50 and a high voltage supply 51 with the associated connections indicated. A more detailed circuit diagram for the blood volume readout circuit is shown in FIG. 7.

In general, the feedback circuitry fulfills two functions. Such circuitry compensates for changes in optical density produced by changes in the blood volume in the tissue being examined during the monitoring and also provides a recordable signal giving a direct measure of these changes. More specifically, the high voltage regulation or "feedback" circuitry provides a signal for controlling the voltage supplying the photomultiplier or other detector, lowering the supply voltage when the reference signal becomes stronger and conversely increasing sensitivity by increasing the voltage when the signal wanes. The level of the reference signal (labeled R) at junction J-1 (FIG. 6) is fed to the high voltage regulation circuit 50 as indicated and such periodic presentation of signal R is controlled by the timing pulse generator 41. Since the reference wavelength is chosen at a hemoglobin isobestic point so as to be sensitive only to blood (hemoglobin) concentration and not to its degree of oxygenation, this mode of operation compensates for changes in blood volume in the transilluminated field and additionally provides a useful measurement of blood volume which can be recorded by means of the blood volume circuit 70, shown in more detail in FIG. 7.

To complete the general description of FIG. 6, the output conditioner circuitry 26 of FIG. 5 includes in FIG. 6 the designated differential amplifier circuitry 60, the time constants circuitry 61 and the logarithmic and output gain amplifier circuitry 62. As those skilled in the art will appreciate from the diagrammatic representation of FIG. 6, the output conditioning circuitry provides the differential signal by subtracting the reference signal (R) from the sample wavelengths $S_1$ and $S_2$ by means of the differential amplifiers 60 and conditions it further by appropriate filtering through time constant circuitry 61 and by further logarithmic and output gain amplifiers 62 to be respectively in units of optical density in conformation with the Beer-Lambert Law and compatible to commonly used recording systems such as strip charts, x-y plotters, oscillographs, or the like.

While not fully illustrated in FIG. 6, those skilled in the art with knowledge of prior art photometric techniques will appreciate that either of two methods may be employed for synchronizing the different wavelength presentations and the detection system. When lasers, LaD's, LED's or similar easily pulsed sources are employed, the timing pulse generator 41 may be employed to control the pulsers of these devices. Alternatively, when incandescent or arc lamp sources are used, a chopping wheel, controlling presentation of light to different filters or monochromators, may be employed to trigger the timing pulse generator 41 by means of a secondary light source and phototransistor assembly activated by a slot in the chopping wheel. In either case, the timing pulse generator 41 controls the FET switches 40 which demodulate the detector output.

Given the conceptual description of the invention as previously set forth, those skilled in the art will immediately visualize various forms of feedback circuitry for monitoring the level of the received reference signal R and providing a corresponding blood volume readout. One such blood volume readout circuitry is diagrammed in FIG. 7 and corresponds to the blood volume circuit 70 indicated in FIG. 6. In FIG. 7, the junction J-2 connects the output of the high voltage supply 51 (FIG. 6) to a voltage divider 80 which in turn at junction J-3 connects to an adjustable time constant circuit 81 and through resistor 82 to a pair of differential amplifiers 85, 86 having respective feedback loops 85', 86', the latter having an adjustable gain 88. Respective coarse zero 90 and fine zero 91 resistor networks provide additional operating adjustments as indicated in FIG. 7. Output 95 provides the desired signal designed to reflect the changes in blood volume to the organ as the same are reflected in changes in the feedback voltage. Mention is again made that either the feedback regulated voltage to the detector or the regulating feedback voltage itself may be recorded as a measure of such blood volume change.

Figure 8:
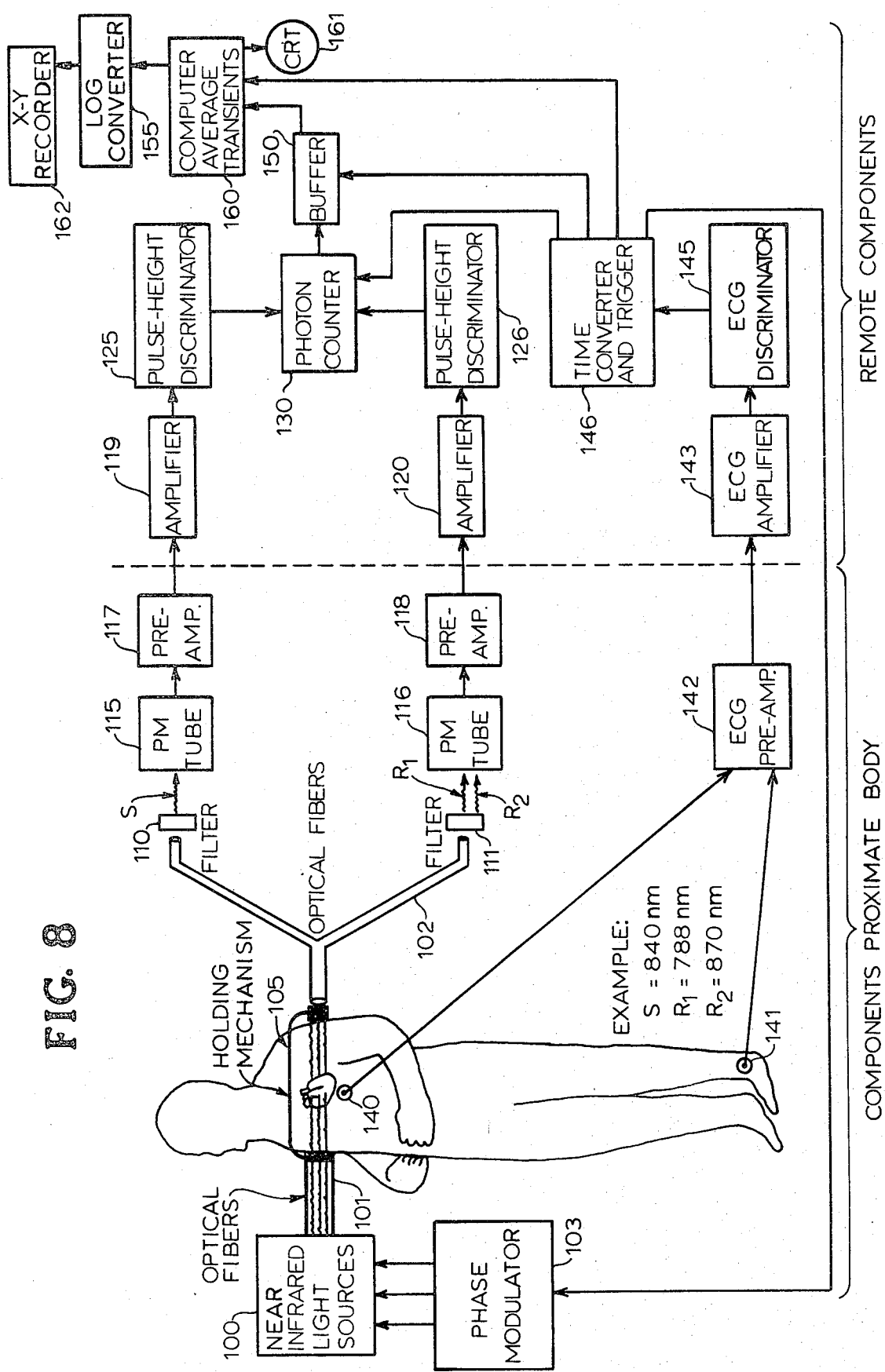
FIG. 8 is a detailed block diagram of a system of instrumentation for carrying out the monitoring techniques in vivo on a pulsating organ, i.e., the heart in situ and for compensating for such pulsations and using counting circuitry.

Versatility of the invention to another application and utilization of digital, photon counting and differential method circuitry are illustrated in FIG. 8. The instrumentation of FIG. 8 does not show common components such as power supplies, and the like, and assumes that the problem to be solved is the examination of oxidative metabolic and $O_2$ sufficiency signals in the beating heart which produces motion artifacts and also may go through changes in beat intervals, i.e., change frequency. The basic mode of operation is that of providing a stroboscopic operation, timed to the cardiac cycle and utilizing a minimum of three wavelengths, one measuring wavelength and two reference ones, straddling the measuring one.

As light sources, laser diodes (LaD's) are preferred because of their narrow bandwidth, small size, sufficiently high but non-hazardous intensity, low voltages, high efficiency, and rapid modulation. Alternatively, light emitting diodes (LED's) may be employed with the advantages of LaD's except for wider bandwidth. Incandescent or arc lamps are less preferred because of lower efficiency, larger size, the need for a means of wavelength selection and a requirement for higher voltages.

As illustrated in FIG. 8, the fiber optics bundle is randomly split into two bundles for the three wavelength system illustrated. While a pair of photomultipliers are shown, the possible configuration of using a single photomultiplier with the housing window pressed directly against the back of the subject is contemplated. In this latter case, the light sources would be used alternately, which is possible at high frequencies of switching so that the heart has not moved significantly between consecutive pulses.

Referring more specifically to FIG. 8, the radiation of three different wavelengths generated by the light sources 100 are transmitted through three optical fibers 101 into the chest. A large full optical fiber bundle 102 receives the transmitted radiation at the other side of the chest and branches into lesser bundles 102′ and 102″. Other fiber optic bundle arrangements could, of course, be employed to effect the light transmission and detection functions being described. An appropriate holding mechanism 105 secures the respective transmitting and receiving optical faces to the subject as shown. Phase modulation circuitry 103 is operated by the time converter and trigger circuitry 146 later referred to.

Much of the instrumentation of FIG. 8 will be understood from description already set forth. However, recognition should be taken, in interpreting FIG. 8, of the basic distinctions involved in applying the invention to monitoring cellular metabolism in vivo, in situ, non-invasively and continuously in the relatively stable size brain as compared to similar monitoring of cellular metabolism in vivo, in situ, non-invasively and continuously of an organ, i.e., the heart, whose physical characteristics change radically in the course of a heart cycle. Nevertheless, as can be seen from FIG. 8, the invention is applicable to both types of situations and makes available a form of non-invasive, in vivo organ and cellular metabolism monitoring never heretofore available.

Continuing with the description of FIG. 8, the light detector system includes two optical interference filters 110, 111, one of which is designed to pass only the measuring wavelength and the other of which is designed to pass the two reference wavelengths. Such system also includes a pair of photomultiplier tubes 115, 116, preamplifiers 117, 118, amplifiers 119, 120, pulse height discriminators 125, 126 and a differential photon counter 130, all of which components are well known and their respective functions in the illustrated circuitry arrangement of FIG. 8 will be understood. However, the means for timing the photon counter 130 in coordination with the heart cycle and for executing a stroboscopic type operation of the system are believed to be unique to the invention and are next explained in more detail.

An electrocardiogram (ECG) is picked up by two standard electrodes 140, 141 on the arm, leg, or chest, whichever is most useful and convenient and is amplified by an appropriate preamplifier 142 which should be close to the patient, and an amplifier 143 which may be more remote. An appropriate feature of the ECG is selected by the ECG discriminator 145 to provide a trigger for subsequent circuitry through the indicated time converter and trigger circuitry 146. Such selected feature can be any easily and uniquely distinguishable wave property, such as peak height, rate of rise or the like. Subsequently, the "Real Time to Cardiac Time Converter" forming part of the time converter and trigger circuit 146 measures the time interval between sequential trigger events and digitally divides this period into a standard number of units, say 100. Advantage is taken of the observation that since the mechanical events, and therefore motion of the heart, are mostly fixed within the cardiac cycle no matter what the beat frequency, the various mechanical events occur at a constant interval period within the cycle. In other words, they are time locked to the ECG, not to real time.

The cardiac time information is used in one of two ways. If optical information is desired on the entire cardiac cycle, the differential photon counts may be stored in a temporary digital memory, i.e., buffer 150, and read out in the fixed 100 time intervals calculated for that beat by the time converter portion of the time converter and trigger circuit 146. In another mode of operation, the solid state light sources can be activated for short periods only to coincide approximately with the most significant time periods within one beat, programmed in cardiac time of the previous beat. Subsequently, the exact intervals can be selected and read out of the buffer 150 as described before. An important advantage of buffer operation keyed in terms of cardiac time of that particular beat is the ability to reject information derived from cycles aborted by the occurrence of extra-systoles. Recording and display of the information can be accomplished in a variety of ways such as by a chart recorder, line printer or on paper tape punch. Continuous monitoring as a factor of time can be performed for selected mechanical positions, say, full relaxation and full contraction. In addition, the information on complete cycles can be stored and manipulated as by the computer for average transient 160 in order to improve signal to noise ratio and displayed on the cathode ray tube CRT 161 or passed through log converter 155 and read out on X-Y plotter 162.

While the illustrated system utilizing dual photometers allows substantial flexibility in timing, the invention contemplates employment of a single photomultiplier with the housing window pressed directly against the back. In this application, means are provided for using the light sources alternately which is possible at high frequencies of switching so that the heart has not moved significantly.

Figures 9A, 9B, 9C:
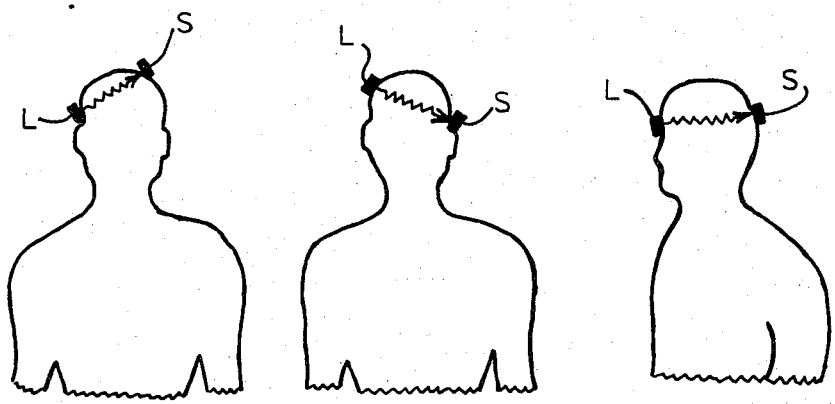
FIGS. 9A, 9B, and 9C illustrate alternative positioning of the light sources (L) and sensors (S) on the head
Figure 9D:
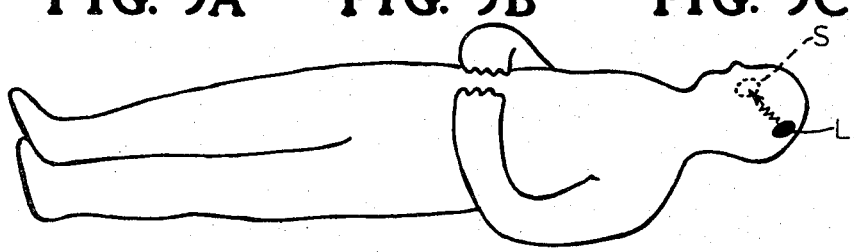
FIG. 9D illustrates positioning of the light sources and sensor with the body reclined.

Also to be understood is the fact that the exact placement of the light source and sensor on the body will depend on what organ or portion of the body is of interest at the moment. Thus, as illustrated in FIGS. 9A, 9B, and 9C the light source, designated L, and the light receiver, designated S, may be in various positions on the head and with the head upright or as in the case of bed ridden patient or in a patient being examined prone, the orientation of patient, light source and receiver could be as illustrated in FIG. 9D.

Throughout the circuit description, no attempt has been made to indicate all of the various standard components such as power supplies, and the like. Essentially all of the major components of the illustrated circuitry are known and their individual construction and functions are known. Further, given the broad instrumentation concepts illustrated in FIGS. 5-8, it is believed those skilled in the art will immediately recognize the organization and functioning of all of the illustrated components and will see other known circuit devices that might be employed to carry out the invention as herein explained.

TOMOGRAPHY

Figure 10:
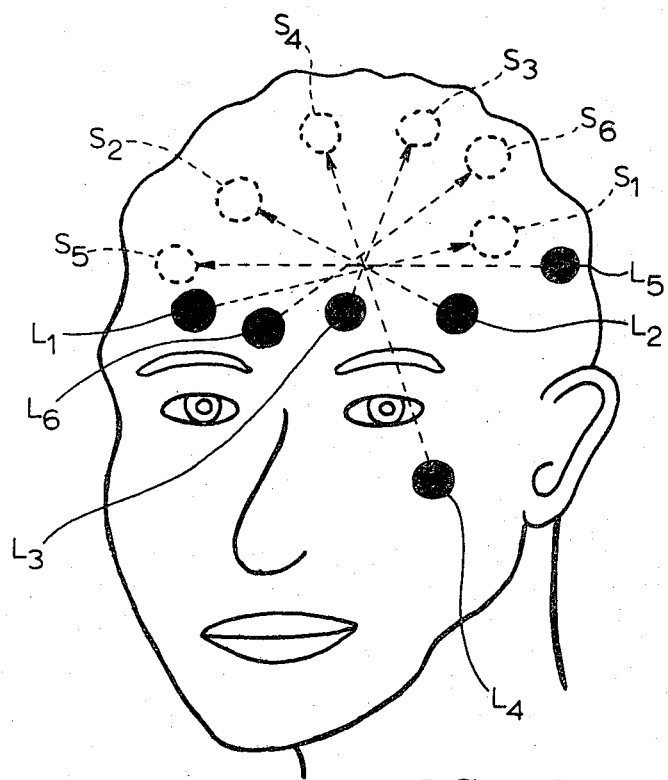
FIG. 10 illustrates application of the invention to a tomography-like technique.
Figure 11:
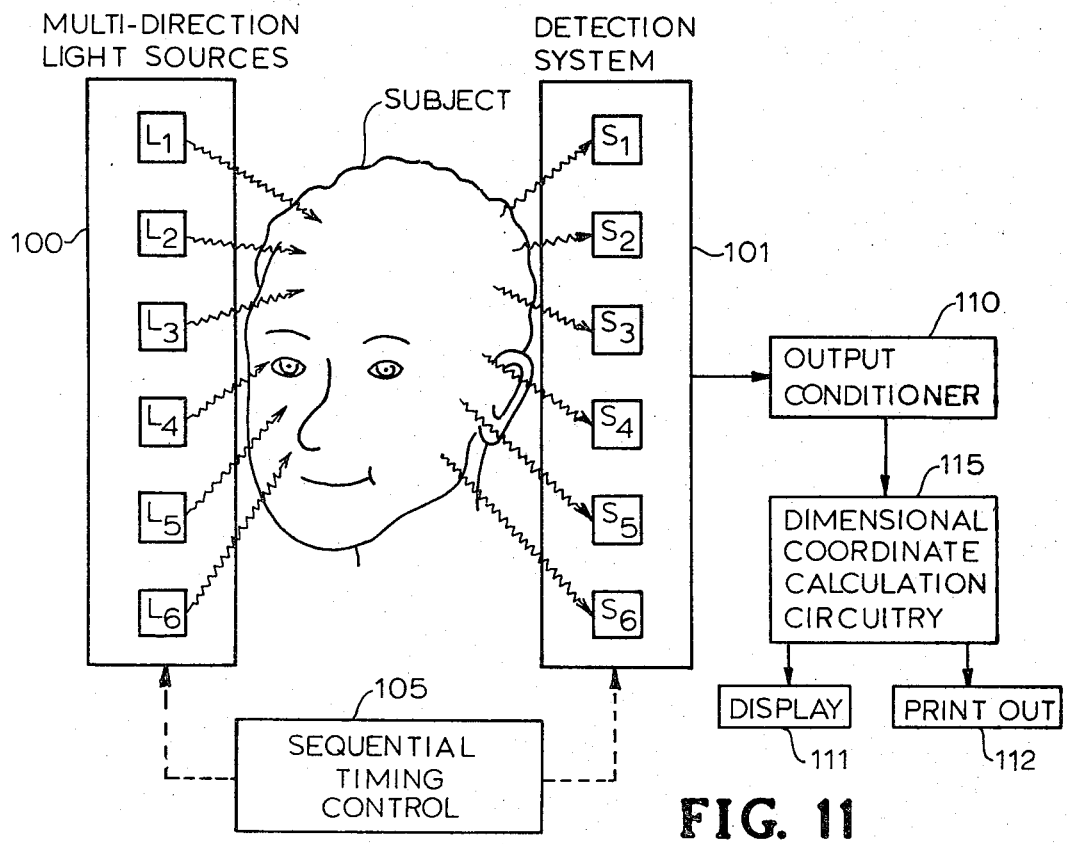
FIG. 11 is a schematic diagram of an axial tomography system according to the invention.

For localization of areas of infarct, stroke, oligemia and ischemia or other pathological changes in cellular oxidative metabolism the known techniques of axial tomography are applicable. FIG. 10 schematically illustrates how paired light sources and sensors can be located to establish optical paths in different planes, at different angles and the like. That is, by using multi-directional transillumination of the organ according to the invention, calculation of the appropriate wavelength intensity difference in 2 and 3 dimensional coordinates will reveal the location, size, and shape of the afflicted area. FIG. 11 schematically illustrates the general circuitry arrangement.

Tomographic procedures have been applied in connection with X-ray photography and more recently by employing an X-ray scanning technique. In the latter technique, the patient's head is irradiated with coherent beams of X-rays from a source to a detector. Both rotate stepwise around the patients head and intensity of radiation is recorded for each set of coordinates. Information on intensity is recorded and analyzed for a two dimensional plane by means of a small, dedicated computer. A complete scan in one plane requires fifteen to twenty minutes. Additional planes, for extension toward three dimensional localization and description, need equal exposure times. The limiting difficulty is the strain on the patient in keeping his head immobilized for these extended periods of time.

In practicing tomographic techniques in accordance with the present invention, light sources 100 in the 700-1300 nm near infrared region and providing a plane of light such as continuous wave laser diodes as an example, are used for brief, sequential multi-directional transillumination toward a number of detectors located in the detection system 101 on the opposite side of the head, chest or other region of the body as illustrated by FIG. 10. A sequential timing control 105 such as a ring counter or the like is used for sequentially energizing the light sources L1-L6 in coordination with the sensing. U.S. Pat. No. 3,910,701 illustrates one system for sequentially energizing six light emitting diodes. An appropriate output conditioner circuit 110 receives the output and passes the same to a display 111 or print out 112 through a dimensional coordinate calculation circuitry as illustrated and as indicated by established tomography techniques. By the application of a complete set of detectors around the body part to be transilluminated and a limited number of measuring and reference sources, (e.g., six), as seen in FIG. 10, exposure times can be decreased by at least a factor of ten and probably more. In addition, the information will be obtained non-invasively, in vivo, in situ and atraumatically. Such information will directly indicate the areas of oxygen insufficiency or impairment of blood flow or other conditions accompanied by a change in cellular oxidative metabolism, e.g., tumors. Finally, the near infrared radiation at the power levels and optical densities employed has no cumulative deleterious effects as is the case with X-ray irradiation.

In summary, there has been disclosed what is believed to be a basically new approach to monitoring cellular metabolism in a living organ and more specifically to monitoring cellular oxidative metabolism in vivo, in situ, non-invasively and continuously in a manner not heretofore accomplished and productive of much useful information for the health of the patient. Those skilled in the art will also appreciate the forms of display available for the information of interest such as by recorder, oscilloscope, tape, printer, or the like.

By the terms "organ metabolism", "cellular metabolism", "cellular oxidative metabolism", "metabolic activity", and the like, as used herein and in the appended claims as being "information" of interest, there is meant the sum of all physical and chemical processes by which energy is made available for use by the organ. Circulatory processes by which the required metabolites are transported to cellular reaction sites are deemed to be included in such terminology as well as the metabolic reactions within the cells of the organ. The broad concept of examining with one measuring wavelength a cellular activity, e.g., cytochrome a, $a_3$ oxygenation, related to a transmission characteristic of such wavelength and the same activity with at least one other reference wavelength of different characteristic and comparing the respective transmitted wavelength intensities as a difference or ratio as a measure of such activity, it is believed with hereafter suggest many as yet unpredictable applications of such concept.

Of particular value in the application of the invention is that unlike hazardous surgical laser apparatus and the like, the method and apparatus of the invention operates well below hazardous light levels known to cause thermal, photochemical or other damaging tissue reactions. The accepted laser safety standard (American National Standard 136.1-1976) for the near infrared range allows a Maximum Permissible Exposure (MPE) for skin exposure to a laser beam of 100 milliwatts per square centimeter average power for multiple pulse exposure periods longer than 10 seconds. As a comparison, the presently performed experiments have not employed more than 2.8 milliwatts per square centimeter time average power, i.e., approximately 35 times less than the MPE. Successful experiments have been performed with substantially less intensities.

Finally, it is noted that the illustrated tomographic technique in itself suggests many new applications for localization of information since the need for such information is so widespread. While the illustrations show plural sets of light sources it should also be understood that a single set of measuring and wavelengths could be employed and sequentially physically directed to various optical paths or the organ of interest could be scanned by moving the light sources and detectors relative to the body in the manner of the X-ray scanning mentioned above.

I claim:

1. A spectrophotometric method for measuring local metabolism of a body organ such as the brain in situ, in vivo, non-invasively, atraumatically, harmlessly, rapidly and continuously, said method comprising the steps:

(a) with the organ positioned in the body in vivo, selecting an optical path intersecting said organ and extending for several centimeters between points of light entry and exit on the surface of the body;

(b) establishing a plurality of near infrared light sources located external of the body and having light emissions of different wavelength in the 700 to 1300 nanometer spectral range and of an intensity below the level damaging to the body and said organ as positioned in the body in vivo but sufficient to be detectable by a light sensor after transmission along said path, said emissions including at least one measuring wavelength and at least one reference wavelength within said spectral range, each said measuring wavelength being selected such that said organ in vivo exhibits a selective absorption therefor, the extent of which is dependent upon a specific state of metabolic activity of said organ in vivo;

(c) directing said light emissions at said measuring and reference wavelengths sequentially along said path and through said organ and receiving the transmitted light emissions at a light sensor and circuit means to produce an electrical output signal representing the difference in absorption of said measuring and reference wavelengths by the organ as a function of the state of said metabolic activity in vivo; and (d) converting said electrical output signal to a signal providing a substantially continuous and rapid measure of said activity.

2. The method of claim 1 wherein each respective said measuring wavelength is selected within an absorption band of a metabolite, enzyme or other cellular biochemical entity controlling said state of activity and wherein each said reference wavelength to which a respective measuring wavelength is referred is selected so as to be more distant from the peak of the respective said band within which such respective wavelength resides.

3. The method of claim 1 wherein said optical path is linear and said points of light entry and exit are at opposed positions on said body.

4. The method of claim 1 wherein said activity is one of cellular metabolism.

5. The method of claim 4 wherein said activity is that of the redox state of enzyme cytochrome a, $a_3$.

6. The method of claim 1 wherein said activity is that of hemoglobin oxygenation in said organ.

7. The method of claim 1 wherein said activity relates to local changes in blood volume in said organ.

8. The method of claim 1 including the step of periodically interrupting normal measuring of said metabolism by admitting an agent to said body in a manner enabling such agent to reach said organ and designed to effect a fluctuating change of the absorption properties within said organ over a period of time effecting a corresponding change in said electrical output signal during such time, and recording the intensity of said fluctuating change and the time interval between the beginning and end of said change in the output signal brought about by said agent within said organ as a measure of the blood flow rate to said organ.

9. The method of claim 8 wherein said agent comprises a dye agent.

10. The method of claim 8 wherein said agent comprises a gaseous agent.

11. The method of claim 1 wherein said organ is the heart.

12. The method of claim 1 wherein said activity is that of hemoglobin oxygenation in said organ.

13. The method of claim 1 wherein said activity is that of the redox state of enzyme cytochrome a, $a_3$ in said organ.

14. The method of claim 1 wherein said activity includes both the redox state of enzyme cytochrome a, $a_3$ in said organ and the state of hemoglobin oxygenation in said organ, said plural light sources including one measuring wavelength in an absorption band having a peak related to said redox state of enzyme cytochrome a, $a_3$ and another measuring wavelength in an absorption band having a peak related to said hemoglobin oxygenation and at least one said reference wavelength referable to both measuring wavelengths and operating said sensor and circuit means to produce one electrical output signal for conversion and recording as a measure of said redox state of enzyme cytochrome a, $a_3$ and another electrical output signal for conversion and recording as a measure of said hemoglobin oxygenation.

15. The method of claim 14 wherein one said measuring length is $840\pm15$ nanometers for purposes of measuring said redox state of enzyme cytochrome a, $a_3$ and another said measuring length is $760\pm20$ nanometers for purposes of measuring said state of hemoglobin oxygenation.

16. The method of claim 1 wherein at least one said measuring wavelength is $760\pm20$ nanometers and at least one said reference wavelength is an isobestic point for oxygenated and disoxygenated hemoglobin and including the steps of producing said electrical output signal from prior signals corresponding to the respective optical densities of each wavelength and maintaining substantially constant the level of signal corresponding to the optical density of said reference wavelength by voltage feedback to said sensor means and converting the fluctuating voltage of said feedback to an additional signal for recording as a measure of the blood volume to said organ.

17. The method of claim 1 including at least two said reference wavelengths comprising a contrabestic pair or series.

18. The method of claim 1 including the step of introducing into said body during said measuring a compound having the characteristic of differential optical properties in said spectral range affected by the state of said activity when in said organ.

19. The method of claim 1 wherein said organ is the brain.

20. The spectrophotometric method of measuring a local metabolic function of an organ such as the brain of a body in vivo, in situ, non-invasively, harmlessly, rapidly, continuously and atraumatically comprising the steps:

(a) with the organ positioned in the body in vivo, selecting an optical path intersecting said organ and extending for several centimeters between fixed points of light entry and exit on the surface of the body;

(b) establishing a plurality of light sources located externally of the body and having light emissions of different wavelength including at least one measuring wavelength and one reference wavelength, said measuring wavelength characterized by being selected such that said organ in vivo exhibits a selective absorption therefor, the extent of which is dependent upon a specific state of metabolic activity of said organ in vivo and said reference wavelength being selected sufficiently close to said measuring wavelength to be useful as a reference therefor;

(c) directing said light emissions at said measuring and reference wavelengths sequentially to said point of entry to be transmitted along said path to said point of exit and at a level of intensity below the level damaging to the body and said organ in vivo but sufficient to be detectable by a light sensor after transmission along said path;

(d) receiving the transmitted light emissions at a light sensor and circuit means to produce an electrical output signal representing the difference in absorption of said measuring and reference wavelengths by the organ as a function of the state of said metabolic activity in vivo; and (e) converting said electrical output signal to a signal providing a substantially continuous and rapid measure of said function.

21. The method of measuring according to claim 20, including the step of monitoring the level of sensor signal intensity of said reference wavelength, developing with said light sensor and circuit means a voltage signal corresponding thereto, utilizing said voltage signal as a feedback control for maintaining said reference wavelength sensor signal intensity at some predetermined level and monitoring said feedback voltage signal as a substantially continuous and rapid measure of blood volume of said organ.

22. The method of claim 20 including the step of periodically interrupting normal measuring of said metabolism by admitting an agent to said body in a manner enabling such agent to reach said organ and designed to effect a fluctuating change of the absorption properties within said organ over a period of time effecting a corresponding change in said electrical output signal during such time, and recording the intensity of said fluctuating change and the time interval between the beginning and end of said change in the output signal brought about by said agent within said organ as a measure of the blood flow rate to said organ.

23. A spectrophotometric method for monitoring the local oxygen sufficiency of a body organ such as the brain in vivo, in situ, non-invasively, atraumatically, harmlessly, rapidly and continuously, said method comprising the steps:
(a) providing means for producing near infrared light at different wavelengths in the 700 to 1300 nanometer range and of sufficient intensity to be detectable after transmission along an optical path of several centimeters extending through the body and intersecting said organ but with said intensity being below that which would damage any in vivo body material included in said path;
(b) selecting at least two measuring wavelengths and at least one reference wavelength within said spectral region for transmission through the body organ to be monitored, each said measuring wavelength being selected from within one of the absorption bands of oxidized cytochrome a, $a_3$ and disoxygenated hemoglobin, and each said reference wavelength being selected from a spectral region within from about 75 nanometers on either side of a measuring wavelength;
(c) with the organ positioned in the body in vivo, locating and fixing the body and said organ with relation to said light means in a position suited for transillumination therethrough along an optical path of several centimeters extending through said body and intersecting said organ;
(d) causing beams of light at each measuring and reference wavelength to be focused in alternating sequence on one side of the body so as to effect entry therein and passage along said path through said body intersecting said organ and then to a point of exit from said body;
(e) detecting the light emerging from said body at the point of exit therefrom and electrically converting the received light intensity to an output signal for each measuring wavelength compared to a selected reference wavelength and representing the difference in absorption as a function of the different wavelengths compared; and
(f) electrically converting each such output signal to a signal as a substantially continuous and rapid representation of said oxygen sufficiency of said organ in vivo.

24. The method in accordance with claim 23 wherein the Hb-HbO$_2$ isobestic point at 815±5 nanometers is selected as the reference wavelength.

25. The method in accordance with claim 23 wherein a measuring wavelength at 840±15 nanometers and a reference wavelength at 815±5 nanometers are used to monitor the redox state of the cellular enzyme cytochrome a, $a_3$.

26. The method in accordance with claim 23 wherein a measuring wavelength at 760±20 nanometers and a reference wavelength at 815±5 nanometers are used to monitor the oxygenation state of hemoglobin.

27. The method in accordance with claim 23 including at least two said reference wavelengths comprising a contrabestic pair or series.

28. A spectrophotometric method for monitoring local changes in blood volume and in metabolism as indicated in the redox state of cytochrome a, $a_3$ and the oxygenation state of homoglobin in an intact organ such as the brain of the human or animal body and wherein said monitoring is accomplished in vivo, in situ, harmlessly, rapidly, continuously and atraumatically, said method comprising:
(a) providing a first source of near infrared light having a wavelength in the absorption band of oxidized cytochrome a, $a_3$, a second source of such light having a wavelength in the absorption band of disoxygenated hemoglobin and a third source having a wavelength at the 815±5 nanometers isobestic point of hemoglobin, the latter wavelength being selected to provide a reference against which the others may be measured;
(b) with the organ positioned in the body in vivo, directing the separate wavelengths of said near infrared light in alternating sequence and at a level of intensity below that which would be damaging to the body and organ in vivo at one fixed entry point on the body under test so as to effect an optical pathway into and through the organ and then to a fixed point of exit several centimeters therefrom elsewhere on the body;
(c) detecting the light emerging from said body after passage through said organ by means of electrically operated photon sensor means having a voltage supply controlled by a feedback circuit;
(d) converting the detected light energy into electrical signals for each wavelength while regulating changes in the voltage supply of said photon sensor means to maintain a constant signal at the reference wavelength;
(e) measuring the intensity of said electrical signals and determining the quantitative differences in intensity between the measuring and reference signals;
(f) converting said differences to corresponding optical density values; and
(g) continuously recording said optical density values as a substantially continuous and rapid measure of said metabolism in vivo together with the changes in the voltage supplied to said photon sensor means as a substantially continuous and rapid measure of said blood volume in vivo.

29. The method in accordance with claim 28 wherein a wavelength at about 840 nanometers is used to monitor the redox state of cytochrome a, $a_3$.

30. The method in accordance with claim 28 wherein a wavelength at about 760 nanometers is used to monitor the oxygenation state of hemoglobin.

31. The method in accordance with claim 28 wherein the organ monitored is the heart.

32. The method in accordance with claim 28 wherein the organ monitored is the brain.

33. A spectrophotometric method for continuously, in vivo, in situ, harmlessly, rapidly and atraumatically monitoring local changes in blood volume and in metabolism as indicated in the redox state of cytochrome a, $a_3$ and the oxygenation state of hemoglobin in an intact organ such as the brain of the human or animal body, said method comprising:

(a) providing a first source of near infrared light having a wavelength in the absorption band of oxidized cytochrome a, $a_3$, a second source of such light having a wavelength in the absorption band of disoxygenated hemoglobin and a third source having a wavelength at the 815±5 nanometers isobestic point of hemoglobin, the latter wavelength being selected to provide a reference against which the others may be measured;

(b) with the organ positioned in the body in vivo, directing the separate wavelengths of said near infrared light in alternating sequence at a level of intensity below that which would be damaging to the organ in vivo and to a fixed point of entry on the body under test so as to effect an optical pathway of at least 4 centimeters in length into and through the organ and to a fixed point of exit elsewhere on the body;

(c) detecting the light emerging from said body after passage through said organ;

(d) measuring the detected light for each of the separate wavelengths by means of photon counter means;

(e) determining the quantitative differences in intensity between the light measured at the measuring and reference wavelengths;

(f) converting said differences to corresponding optical density values; and (g) recording said optical density values together with the changes in the optical density values at the reference wavelength.

34. The method in accordance with claim 33 wherein a wavelength at about 840 nanometers is used to monitor the redox state of cytochrome a, $a_3$.

35. The method in accordance with claim 33, wherein a wavelength at about 760 nm is used to monitor the oxygenation state of hemoglobin.

36. The method in accordance with claim 33 wherein the organ monitored is the heart.

37. The method in accordance with claim 33 wherein the organ monitored is the brain.

38. Apparatus for measuring metabolism of a body organ such as the brain in situ, in vivo, non-invasively, atraumatically, harmlessly, rapidly and continuously comprising:

(a) a plurality of near infrared light sources located external of the body and having light emissions of different wavelength in the 700 to 1300 nanometer spectral range and of an intensity below the level damaging to the body and said organ in vivo but sufficient to be detectable by a light sensor after transmission along an optical path extending for several centimeters between a pair of points of light source attachment and sensor attachment on the surface of the body and intersecting said organ;

(b) means for sequentially operating said light sources to produce at least one measuring wavelength and at least one reference wavelength within said spectral range for transmission along said path and through said organ and at levels of intensity below that which would be damaging to the body and said organ in vivo, each said measuring length being of a value for which said organ in vivo exhibits an absorption band for a specific state of metabolic activity, the absorption peak of which changes as said in vivo state of activity changes, said measuring wavelength being of a value to reside within said band and closer to said peak than said reference wavelength;

(c) attachment means for fixing the output of said light sources to a selected fixed light entry point on said body enabling transmission of said light emissions from said light sources along said path and through said organ such that the absorption thereof becomes dependent upon the in vivo state of said metabolic activity of said organ;

(d) means for receiving the transmitted light emissions including a light sensor fixed to a selected fixed light exit point on said body spaced along said path several centimeters from said entry point and circuit means to produce for each wavelength a reference signal corresponding to the optical density thereof at said sensor and to produce from such reference signals an electrical output representing the difference in absorption of the organ as a function of each respective set of compared measuring and reference wavelengths and the in vivo state of said metabolic activity in said organ; and (e) means for receiving said electrical output and converting the same to a signal providing a substantially continuous and rapid measure of said activity.

(e) means for receiving said electrical output and converting the same to a signal to be displayed as a measure of said activity.

39. The apparatus of claim 38 wherein said optical path is intended to be linear and said light source attachment means and said light sensor fixation are adapted for opposed positions on said body.

40. The apparatus of claim 38 wherein said activity is one of cellular metabolism and said wavelengths operate in reference.

41. The apparatus of claim 38 wherein said activity is one of cellular oxidative metabolism and said wavelengths operate in reference thereto.

42. The apparatus of claim 41 wherein said activity is that of the redox state of enzyme cytochrome a, $a_3$ and said wavelengths operate in reference thereto.

43. The apparatus of claim 38 wherein said activity is that of hemoglobin oxygenation in said organ and said wavelengths operate in reference thereto.

44. The apparatus of claim 38 wherein said activity is that of local changes in blood volume in said organ including means for establishing a feedback voltage to maintain at some predetermined level the said reference signal corresponding to a selected said reference wavelength and monitoring said voltage as a measure of said volume.

45. The apparatus of claim 38 wherein said organ is the heart of said body and including means for monitoring the heart beat of said body and triggering said light sources such that said transmitting is accomplished at selected times in rhythm with a selected state of the heart of said body.

46. The apparatus of claim 38 wherein said measured activity is that of the redox state of enzyme cytochrome a, a₃ in said organ.

47. The apparatus of claim 38 wherein said measured activity is that of hemoglobin oxygenation in said organ.

48. The apparatus of claim 38 wherein said measured activity includes both the redox state of enzyme cytochrome a, a₃ and the state of hemoglobin oxygenation in said organ, said plural light sources include one measuring wavelength in an absorption band related to said redox state of enzyme cytochrome a, a₃ and another measuring wavelength in an absorption band related to said hemoglobin oxygenation and at least one said reference wavelength referable to both measuring wavelengths, said signal receiving and converting means being adapted to producing one output signal for conversion to provide a substantially continuous and rapid measure of said redox state of enzyme cytochrome a, a₃ and another output signal for conversion to provide a substantially continuous and rapid measure of said hemoglobin oxygenation.

49. The apparatus of claim 48 wherein one said measuring wavelength is 840±15 nanometers for purposes of measuring said redox state of enzyme cytochrome a, a₃ and another said measuring wavelength is 760±20 nanometers for purposes of measuring said hemoglobin oxygenation.

50. The apparatus of claim 50 wherein said measuring wavelength is 760±20 nanometers and said reference wavelength corresponds with an isobestic point for oxygenated and disoxygenated hemoglobin and including means for maintaining substantially constant the level of received signal corresponding to said reference wavelength by voltage feedback to said sensor means and converting the fluctuating voltage of said feedback to an additional signal for display as a measure of the blood volume to said organ.

51. The apparatus of claim 37 wherein said light sources and means for operating said light sources are adapted to produce a pair of said reference wavelengths comprising a contrabestic pair.

52. Apparatus for measuring a local metabolic oxygen dependent function of an organ such as the brain of a body in situ, in vivo, non-invasively, atraumatically, harmlessly, rapidly and continuously where such function bears a measurable relation to an oxygen dependent absorption characteristic of the organ in vivo for a particular wavelength of light transmitted therethrough, comprising:
(a) a source of light productive of a wavelength within the range of 700 to 1300 nanometers and of a value for which said organ in vivo exhibits an absorption band for a specific state of an oxygen dependent metabolic activity the absorption peak of which changes as said in vivo state of activity changes with variations in oxygen supply to said organ, said light being of sufficient intensity to penetrate and pass through said body along an optical path of several centimeters length which includes such organ but below that level of intensity which would damage said organ in vivo or any in vivo portion of the body included in said path;
(b) means for directing said light along a said path of several centimeters length from a place of entry on said body through said organ and to another place of exit on said body; and
(c) means for receiving the transmitted light with sensor and circuit means and developing therewith for display a signal representative of the state of said oxygen dependent activity.

53. A spectrophotometric apparatus for monitoring the local oxygen sufficiency of a body organ such as the brain in vivo, in situ, non-invasively, atraumatically, harmlessly, rapidly and continuously, comprising:
(a) means for producing near infrared light at different wavelengths in the 700 to 1300 nanometer range and of sufficient intensity to be detectable after transmission for several centimeters along an optical path extending through the body and intersecting said organ but with said intensity being below that which would damage said organ in vivo or any in vivo portion of said body included in said path;
(b) means for selecting at least one measuring wavelength and at least one reference wavelength within said spectral region for transmission through the in vivo body organ to be monitored, each said measuring wavelength being selected from within one of the absorption bands of oxidized cytochrome a,a₃ and disoxygenated hemoglobin, and each said reference wavelength being selected from a spectral region within from about 75 nanometers on either side of a measuring wavelength;
(c) means for locating and fixing the in vivo body and said organ with relation to said light means in a position suited for transillumination therethrough along an optical path of several centimeters length extending through said body and intersecting said organ;
(d) means for directing said light at each measuring and reference wavelength and in alternating sequence to one location on the body so as to effect entry therein and passage along a said path of several centimeters length through said body intersecting said organ and then to a point of exit from said body;
(e) means for detecting the light emerging from said body at the point of exit therefrom, comparing measuring and reference wavelength intensities and electrically converting the received light to an output signal for each measuring and reference wavelength compared and representing the difference in absorption thereof by said organ in vivo as a function of the different wavelengths; and
(f) means for converting each such output signal to a signal substantially continuously and rapidly representative of the changes in the absorption band to which the respective measuring-reference wavelengths are related.

54. The apparatus of claim 50 wherein the Hb-HbO₂ isobestic point at 815+5 nanometers comprises a said reference wavelength.

55. The apparatus of claim 54 wherein one said measuring wavelength comprises 840+15 nanometers and one said reference wavelength comprises 815+5 nanometers and being operative to monitor the redox state of the cellular enzyme cytochrome a, a₃.

56. The apparatus of claim 54 wherein one said measuring wavelength comprises 760+20 nanometers and one said reference wavelength comprises 815+5 nanometers and being operative to monitor the oxygenation state of hemoglobin.

57. A spectrophotometric apparatus for monitoring local changes in blood volume, the redox state of cytochrome a, $a_3$ and the oxygenation state of hemoglobin in an intact organ such as the brain of the human or animal body and wherein said monitoring is accomplished in vivo, in situ, harmlessly, rapidly, continuously and atraumatically, comprising:
(a) plural light sources including a first source of near infrared light having a wavelength in the absorption band of oxidized cytochrome a, $a_3$, a second source of such light having a wavelength in the absorption band of disoxygenated hemoglobin and a third source having a wavelength at the 815+5 nanometers isobestic point of hemoglobin, the latter wavelength being selected to provide a reference against which the others may be measured;
(b) means for directing the separate wavelengths of said near infrared light in alternating sequence to the in vivo body under test so as to effect an optical pathway of several centimeters length which enters the body, passes through the organ and emerges from the body
(c) means for detecting the light emerging from said body after passage through said organ including photon sensor means having a voltage supply controlled by a feedback circuit;
(d) means for converting the detected light energy into electrical signals while regulating changes in the voltage supply of said photon sensor means to maintain a constant signal at the reference wavelength;
(e) means for measuring the intensity of said electrical signals, determining the quantitative differences in intensity between the measuring and reference signals and converting said differences to corresponding optical density values; and
(f) means for recording said optical density values together with the changes in the voltage supplied to said photon sensor means.

58. The apparatus of claim 57 wherein said wavelength at about 840 nanometers is operative to monitor the redox state of cytochrome a, $a_3$.

59. The apparatus of claim 57 wherein said wavelength at about 760 nanometers is operative to monitor the oxygenation state of hemoglobin.

60. The apparatus of claim 57 wherein said light sources and said means are adapted for monitoring the heart as said organ.

61. The apparatus of claim 57 wherein said light sources and said means are adapted for monitoring the brain as said organ.

62. A spectrophotometric method for localization of an area of pathological change in metabolism of a body organ such as the brain by measuring local metabolism in selected areas thereof in situ, in vivo, non-invasively, atraumatically, harmlessly, rapidly and continuously, said method comprising the steps:
(a) with the organ positioned in the body in vivo, selecting a plurality of optical paths of several centimeters length intersecting various areas of said organ and extending between various separate three dimensionally located points of entry and exit on the surface of the body;
(b) establishing light source means external of the body and having light emissions of different wavelength and of an intensity below the level damaging to the body and said organ in vivo but sufficient to be detectable by a light sensor after transmission along a said path, said emissions including at least one measuring wavelength and at least one reference wavelength within some spectral range, each said measuring wavelength being selected such that said organ in vivo exhibits a selective absorption therefor, the extent of which is dependent upon a specific in vivo state of metabolic activity associated with said organ;
(c) directing said light emissions at said measuring and reference wavelengths along each of said paths in sequence and through the respective areas of said organ intersected thereby and sequentially receiving the transmitted light emissions at respective light sensor and circuit means associated with the said points of exit to produce an electrical output signal for each said path representing the difference in absorption of said measuring and reference wavelengths by the area of the organ transilluminated therewith as a function of the in vivo state of said metabolic activity in each said respective area thereof; and
(d) converting said electrical output signals to a representation of the localization of said area of change in said organ.

63. The method of claim 62 wherein said light emissions are all in the 700 to 1300 nanometer spectral range.

64. The method of claim 63 wherein said light source means are plural and at least one such light source means is fixed relative to said body at each said point of entry and said light sensor means are plural and at least one said light sensor means is fixed relative to said body at each said point of exit.

65. Apparatus for determining localization of an area of pathological change in metabolism of a body organ such as the brain by measuring local metabolism in selected areas thereof in situ, in vivo, non-invasively, atraumatically, harmlessly, rapidly and continuously, comprising:
(a) a near infrared light source means located external of the body and having light emissions of difference wavelength and of an intensity below the level damaging to the body and said organ in vivo but sufficient to be detectable by a light sensor after transmission along an optical path of several centimeters length extending between points of light source entry and exit on the surface of the body and intersecting an area of said organ;
(b) means for operating said light source means to produce in sequence at least one measuring wavelength and at least one reference wavelength suited for transmission along a selected said optical path and through a selected area of said organ and at levels of intensity below that which would be damaging to the body and said organ area in vivo, each said measuring wavelength being of a value for which said organ area in vivo exhibits an absorption band for a specific state of metabolic activity, the absorption peak of which changes as said in vivo state of activity changes, said measuring wavelength being of a value to reside within said band and closer to said peak than said reference wavelength;
(c) light directing means connected to said light source means and enabling the output of said light source means to be directed to a plurality of fixed three dimensionally spaced light entry points on said body in a predetermined sequence for transmission of said light emissions from said light source means for several centimeters along respective said optical paths and sequentially through said areas of said organ intersected by said paths and then from said body to respective points of exit such that the absorption thereof becomes dependent upon the respective in vivo state of said metabolic activity in the respective areas of said organ;

(d) light receiving means adapted for receiving the transmitted light emissions at said points of exit in a predetermined sequence coordinated with the sequential entry at said entry points, said light receiving means including for each point of exit a light sensor and circuit means to produce for each wavelength and sequentially for each point of exit a signal corresponding to the optical density thereof at the respective exit point sensor and to produce from such signals an electrical output for each exit point in sequence representing the difference in absorption of the organ area illuminated with the respective path as a function of each respective set of compared measuring and reference wavelengths transmitted therethrough and the in vivo state of said metabolic activity in the respective area of said organ; and (e) means for sequentially storing and converting said outputs to a representation of location, size and shape of said area of pathological change.

66. The apparatus of claim 65 wherein said light emissions are all in the 700 to 1300 nanometer spectral range.

67. The apparatus of claim 65 wherein said light source means comprise plural light sources each productive of said measuring and reference wavelengths and including means to fix one of said light sources to said body at each said point of entry and wherein said light receiving means includes plural said light sensors and including means to fix one said sensor to said body at each said point of exit.

* * * * *

UNITED STATES PATENT AND TRADEMARK OFFICE
CERTIFICATE OF CORRECTION

PATENT NO. : 4,281,645
DATED : Aug. 4, 1981
INVENTOR(S) : Frans F. Jöbsis

It is certified that error appears in the above—identified patent and that said Letters Patent is hereby corrected as shown below:

In the Abstract, line 11, "a, $a_3$" should be --$\underline{a}$, $\underline{a}_3$--.

Col. 4, lines 45, 46, "a, $a_3$" should be --$\underline{a}$, $\underline{a}_3$--.

Col. 4, line 46, "c" should be --$\underline{c}$--.

Col. 5, line 7, "a, $a_3$" should be --$\underline{a}$, $\underline{a}_3$--.

Col. 5, lines 22, 23, "a, $a_3$" should be --$\underline{a}$, $\underline{a}_3$--.

Col. 5, line 32, "a, $a_3$" should be --$\underline{a}$, $\underline{a}_3$--.

Col. 5, line 35, "a, $a_3$" should be --$\underline{a}$, $\underline{a}_3$--.

Col. 6, line 57, "a, $a_3$" should be --$\underline{a}$, $\underline{a}_3$--.

Col. 6, line 67, "hemoblobin" should be --hemoglobin--.
(Our error)

Col. 7, line 48, "a, $a_3$" should be --$\underline{a}$, $\underline{a}_3$--.

Col. 7, line 58, "a, $a_3$" should be --$\underline{a}$, $\underline{a}_3$--.

Col. 7, line 64, "a, $a_3$" should be --$\underline{a}$, $\underline{a}_3$--.

Col. 8, line 11, "a, $a_3$" should be --$\underline{a}$, $\underline{a}_3$--.

Col. 8, line 14, "a, $a_3$" should be --$\underline{a}$, $\underline{a}_3$--.

Col. 8, line 20, "a, $a_3$" should be --$\underline{a}$, $\underline{a}_3$--.

Col. 8, line 32, "a, $a_3$" should be --$\underline{a}$, $\underline{a}_3$--.

UNITED STATES PATENT AND TRADEMARK OFFICE
CERTIFICATE OF CORRECTION

PATENT NO. : 4,281,645

DATED : Aug. 4, 1981

INVENTOR(S) : Frans F. Jöbsis

It is certified that error appears in the above—identified patent and that said Letters Patent is hereby corrected as shown below:

Col. 9, line 25, "a, $a_3$" should be --$\underline{a}$, $\underline{a}_3$--.

Col. 9, line 49, "a, $a_3$" should be --$\underline{a}$, $\underline{a}_3$--.

Col. 9, line 55, "a, $a_3$" should be --$\underline{a}$, $\underline{a}_3$--.

Col. 10, line 46, "a, $a_3$" should be --$\underline{a}$, $\underline{a}_3$--.

Col. 10, line 65, "a, $a_3$" should be --$\underline{a}$, $\underline{a}_3$--.

Col. 11, line 56, "a, $a_3$" should be --$\underline{a}$, $\underline{a}_3$--.

Col. 12, line 2, "a, $a_3$" should be --$\underline{a}$, $\underline{a}_3$--.

Col. 12, line 3, "a, $a_3$" should be --$\underline{a}$, $\underline{a}_3$--.

Col. 12, line 39, "a, $a_3$" should be --$\underline{a}$, $\underline{a}_3$--.

Col. 12, line 41, "a, $a_3$" should be --$\underline{a}$, $\underline{a}_3$--.

Col. 12, line 43, "a, $a_3$" should be --$\underline{a}$, $\underline{a}_3$--.

Col. 12, line 47, "a, $a_3$" should be --$\underline{a}$, $\underline{a}_3$--.

Col. 12, line 56, "a, $a_3$" should be --$\underline{a}$, $\underline{a}_3$--.

Col. 13, line 38, "system" should be --systems--.

Col. 14, line 46, "a, $a_3$" should be --$\underline{a}$, $\underline{a}_3$--.

Col. 14, lines 49, 50, "a, $a_3$" should be --$\underline{a}$, $\underline{a}_3$--.

UNITED STATES PATENT AND TRADEMARK OFFICE
CERTIFICATE OF CORRECTION

PATENT NO. : 4,281,645  
DATED : Aug. 4, 1981  
INVENTOR(S) : Frans F. Jöbsis

Page 3 of 5

It is certified that error appears in the above—identified patent and that said Letters Patent is hereby corrected as shown below:

Col. 20, line 9, "a, $a_3$" should be --$\underline{a}$, $\underline{a}_3$--.

Col. 20, line 15, "with" should be --will--.

Col. 21, line 30, "a, $a_3$" should be --$\underline{a}$, $\underline{a}_3$--.

Col. 21, line 56, "a, $a_3$" should be --$\underline{a}$, $\underline{a}_3$--.

Col. 21, line 59, "a, $a_3$" should be --$\underline{a}$, $\underline{a}_3$--.

Col. 21, line 64, "a, $a_3$" should be --$\underline{a}$, $\underline{a}_3$--.

Col. 22, line 2, "a, $a_3$" should be --$\underline{a}$, $\underline{a}_3$--.

Col. 22, line 7, "a, $a_3$" should be --$\underline{a}$, $\underline{a}_3$--.

Col. 23, line 45, "a, $a_3$" should be --$\underline{a}$, $\underline{a}_3$--.

Col. 24, line 12, "a, $a_3$" should be --$\underline{a}$, $\underline{a}_3$--.

Col. 24, line 23, "a, $a_3$" should be --$\underline{a}$, $\underline{a}_3$--.

Col. 24, line 31, "a, $a_3$" should be --$\underline{a}$, $\underline{a}_3$--.

Col. 25, line 14, "a, $a_3$" should be --$\underline{a}$, $\underline{a}_3$--.

Col. 25, line 20, "a, $a_3$" should be --$\underline{a}$, $\underline{a}_3$--.

Col. 25, line 51, "a, $a_3$" should be --$\underline{a}$, $\underline{a}_3$--.

Col. 26, beginning with line 43, the second (e) paragraph should be deleted.

UNITED STATES PATENT AND TRADEMARK OFFICE
CERTIFICATE OF CORRECTION

PATENT NO. : 4,281,645
DATED : Aug. 4, 1981
INVENTOR(S) : Frans F. Jöbsis

It is certified that error appears in the above—identified patent and that said Letters Patent is hereby corrected as shown below:

Col. 26, line 52, --thereto-- should be inserted after "reference".

Col. 26, line 57, "a, $a_3$" should be --$\underline{a}$, $\underline{a}_3$--.

Col. 27, line 9, "a, $a_3$" should be --$\underline{a}$, $\underline{a}_3$--.

Col. 27, line 14, "a, $a_3$" should be --$\underline{a}$, $\underline{a}_3$--.

Col. 27, line 17, "a, $a_3$" should be --$\underline{a}$, $\underline{a}_3$--.

Col. 27, line 24, "a, $a_3$" should be --$\underline{a}$, $\underline{a}_3$--.

Col. 27, line 30, "a, $a_3$" should be --$\underline{a}$, $\underline{a}_3$--.

Col. 27, line 31, "a, $a_3$" should be --$\underline{a}$, $\underline{a}_3$--.

Col. 27, line 34, "claim 50" should be --claim 49--.

Col. 28, line 28, "a, $a_3$" should be --$\underline{a}$, $\underline{a}_3$--.

Col. 28, line 30, "withn" should be --within--.

Col. 28, line 60, "815+5" should be --815$\pm$5--.

Col. 28, line 63, "840+15" should be --840$\pm$15--.

Col. 28, line 64, "815+5" should be --815$\pm$5--.

Col. 28, line 66, "a, $a_3$" should be --$\underline{a}$, $\underline{a}_3$--.

Col. 28, line 68, "760+20" should be --760$\pm$20--.

UNITED STATES PATENT AND TRADEMARK OFFICE
CERTIFICATE OF CORRECTION

PATENT NO. : 4,281,645

DATED : Aug. 4, 1981

INVENTOR(S) : Frans F. Jöbsis

It is certified that error appears in the above—identified patent and that said Letters Patent is hereby corrected as shown below:

Col. 29, line 1, "815+5" should be --$815 \pm 5$--.

Col. 29, line 6, "a, $a_3$" should be --$\underline{a}$, $\underline{a}_3$--.

Col. 29, line 13, "a, $a_3$" should be --$\underline{a}$, $\underline{a}_3$--.

Col. 29, line 16, "815+5" should be --$815 \pm 5$--.

Col. 29, line 25, a semicolon should be inserted after "body".

Col. 29, line 45, "a, $a_3$" should be --$\underline{a}$, $\underline{a}_3$--.

Col. 30, line 44, "ence" should be --ent--. (Our error)

Signed and Sealed this

Nineteenth Day of January 1982

[SEAL]

Attest:

Attesting Officer

GERALD J. MOSSINGHOFF

Commissioner of Patents and Trademarks